US008969546B2

(12) United States Patent
Kumar et al.

(10) Patent No.: US 8,969,546 B2
(45) Date of Patent: Mar. 3, 2015

(54) COMPOUNDS USEFUL IN IMAGING AND THERAPY

(75) Inventors: Piyush Kumar, Edmonton (CA); Leonard Wiebe, Edmonton (CA); Alexander McEwan, Edmonton (CA)

(73) Assignees: The Governors of the University of Alberta, Edmonton, Alberta (CA); Alberta Health Services, Edmonton, Alberta (CA)

( * ) Notice: Subject to any disclaimer, the term of this patent is extended or adjusted under 35 U.S.C. 154(b) by 0 days.

(21) Appl. No.: 13/805,862

(22) PCT Filed: Jun. 27, 2011

(86) PCT No.: PCT/CA2011/000751
§ 371 (c)(1),
(2), (4) Date: Mar. 14, 2013

(87) PCT Pub. No.: WO2011/160216
PCT Pub. Date: Dec. 29, 2011

(65) Prior Publication Data
US 2013/0211066 A1 Aug. 15, 2013

Related U.S. Application Data

(60) Provisional application No. 61/358,163, filed on Jun. 24, 2010.

(51) Int. Cl.
*C07H 19/052* (2006.01)
*A61K 51/00* (2006.01)
*A61M 36/14* (2006.01)
*A61K 51/04* (2006.01)
*C08B 37/00* (2006.01)

(52) U.S. Cl.
CPC .......... *C07H 19/052* (2013.01); *A61K 51/0453* (2013.01); *A61K 51/0491* (2013.01); *C08B 37/0057* (2013.01)
USPC ....................................... 536/28.8; 424/1.73

(58) Field of Classification Search
None
See application file for complete search history.

(56) References Cited

FOREIGN PATENT DOCUMENTS

CA 1339130 C 7/1997

OTHER PUBLICATIONS

Kumar et al., Bioorg. Med. Chem., 2010, 18(6), 2255-2264.*
International Search Report and Written Opinion issued on Sep. 19, 2011, in PCT/CA2011/000751.
Beck et al. Pretreatment 18F-FAZA PET Predicts Success of Hypoxia-Directed Radiochemotherapy Using Tirapazamine. J Nucl Med. Jun. 2007;48(6):973-980.
Bentzen et al., Feasibility of Detecting Hypoxia in Experimental Mouse Tumours with 18F-Fluorinated Tracers and Positron Emission Tomography—A Study Evaluating [18F] Fluoromisonidazole and [ 18F]Fluoro-2-deoxy-D-glucose. Acta Oncol. 2000;39(5):629-637.
Brown and Giaccia, The Unique Physiology of Solid Tumors: Opportunities (and Problems) for Cancer Therapy. Cancer Res. Apr. 1, 1998;58(7):1408-1416.
Chapman et al., A Marker for Hypoxic Cells in Tumours with Clinical Applicability. Br J Cancer Apr. 1981;43(4):546-550.
Chapman, Measurement of tumor hypoxia by invasive and non-invasive procedures: a review of recent clinical studies. Radiother Oncol. 1991;20 Suppl 1:13-19.
International Search Report issued in PCT/CA2011/000751 dated Sep. 19, 2011.
Imaging Study in Patients With Cancer of the Head & Neck, Lung, Renal Cell, Brain, Lymphoma and Neuroendocrine Tumours. Alberta Health Services Mar. 2012 http://clinicaltrials.gov/ct/show/NCT00323076.
Hypoxia Imaging With 18F FAZA. Prognostic Impact in Cervical Cancer. Medical University of Vienna, Austria. Oct. 2006 http://clinicaltrials.gov/ct/show/NCT00388687.
Kumar et al., An improved synthesis of alpha-AZA, aalpha-AZP and alpha-AZG, the precursors to clinical markers of tissue hypoxia. Tetrahedron Lett. 2001;42:2077-2078.
Kumar et al., Synthesis of 1-beta-D-(5-deoxy-5-iodoarabinofuranosyl)-2-nitroimidazole (beta-IAZA): A Novel Marker of Tissue Hypoxia. Chem. Pharm Bull (Tokyo) Apr. 2003;51(4):399-403.
Kumar et al., Development of an Economical, Single Step Synthesis of FAZA, a Clinical Hypoxia Marker, and Potential Synthons to Prepare its Positional Analogs. Lett in Drug Design & Develop. 2009;6(1):82-85.
Kumar et al., Fluoroazomycin Arabinoside (FAZA): Synthesis, 2H and 3H-labelling and preliminary biological evaluation of a novel 2-nitroimidazole marker of tissue hypoxia. J Label Comp Radiopharmaceuticals. 1999;42:3-16.
Kumar et al., Synthesis of beta-azomycin nucleosides:1-(beta-D-2-iodo-2-deoxyarabinofuranosyl)-2-nitroimidazole (beta-2-IAZA), a novel marker of tissue hypoxia. Tetrahedron Lett 2002;43(11):4427-4429.
Kumar et al., Microwave-assisted (radio)halogenation of nitroimidazole-based Hypoxia markers. Appl. Radiat Isot. Nov. 2002;57(5): 697-703.

(Continued)

*Primary Examiner* — Traviss C McIntosh, III
(74) *Attorney, Agent, or Firm* — Michael A. Whittaker; Acuity Law Group, P.C.

(57) ABSTRACT

Provided in the following specification are precursors or synthons that are useful for the synthesis of various arabinose based chemical and radiochemical derivatives of nitroimidazole-containing azomycin arabinosides, such as radioiodinated 1-#-D-(5-deoxy-5-[I*]-iodoarabinofuranosyl)-2-nitroimidazole (*IAZA), and radiofluorinated 1-#-D-(5-deoxy-5-[18F]-iodoarabinofuranosyl)-2-nitroimidazole (18FAZA). Such compounds are useful in imaging, therapy, or radiotherapy. Further, various syntheses of said precursors/synthons and the incorporation of said precursors/synthons into kits is provided. The precursors/synthons provided herein allow for an improved and facile manufacturing process for nitroimidazole-containing azomycin arabinosides.

11 Claims, 4 Drawing Sheets

(56) References Cited

OTHER PUBLICATIONS

Kumar et al., Synthesis, radiofluorination, and hypoxia-selective studies of FRAZ: A configurational and positional analogue of the clinical hypoxia marker, [18F]-FAZA. Bioorg Med Chem . Mar. 15, 2010;18(6): 2255-2264.

Kunesch et al., Utilisation de la Guanidine Comme Agent Desacetylant Selectif: une Methode de Desacetylation Instantanee Applicable Aux Sucres. Tetrahedron Lett. 1987;28(31):3569-3572.

Lee and Le, New Developments in Radiation Therapy for Head and Neck Cancer: Intensity Modulated Radiation Therapy and Hypoxia Targeting. Semin Oncol. Jun. 2008;35(3):236-250.

Nakano et al., Synthesis of sulfated glucuronyl glycosphingolipids; carbohydrate epitopes of neural cell-adhesion molecules. Carbohydr Res. Apr. 23, 1993;243(1):43-69.

Nicolau and Webber, Stereocontrolled Total Synthesis of Lipoxins B. Synthesis Jun. 1986;453-461.

Nordsmark et al., The Relationship Between Tumor Oxygenation and Cell Proliferation in Human Soft Tissue Sarcomas. Int J Radiat Oncol Biol Phys. Jul. 1, 1996;35(4):701-708.

Nordsmark et al., Hypoxia in human soft tissue sarcomas: Adverse impact on survival and no association with p53 mutations. Br J Cancer Apr. 20, 2001;84(8):1070-1075.

Nordsmark et al., Prognostic value of tumor oxygenation in 397 head and neck tumors after primary radiation therapy. An international multi-center study. Radiother Oncol. Oct. 2005;77(1):18-24.

Nunn et al., Nitroimidazoles and imaging hypoxia. Eur J Nucl Med. Mar. 1995:22(3):265-280.

Piert et al., Hypoxia-Specific Tumor Imaging with 18F-Fluoroazomycin Arabinoside. J Nucl Med. Jan. 2005;46(1):106-113.

Postema et al., Initial results of hypoxia imaging using 1-alpha-D-(5-deoxy-5[18F]-fluoroarabinofuranosyl)-2-nitroimidazole (18F-FAZA). Eur J Nucl Med Mol Imaging Oct. 2009;36(10):1565-1573.

Reischl et al., Preparation of the hypoxia imaging PET tracer [18F]FAZA: reaction parameters and automation. Appl Radiat. Isot. Jun. 2005;62(6):897-901.

Sorger et al., [18F]Fluoroazomycinarabinofuranoside (18FAZA) and [18F]Fluoromisonidazole (18FMISO): A comparative study of their selective uptake in hypoxic cells and PET imaging in experimental rat tumors. Nucl Med Biol. Apr. 2003;30(3):317-326.

Souvatzoglou et al., Tumour hypoxia imaging with [18F]FAZA PET in head and neck cancer patients: a pilot study. Eur J Nucl Med Mol Imaging Oct. 2007:34(10)1566-1575.

Tubis et al., Labeled Metronidazoles as Potential New Agents for Amebic Hepatic Abscess Imaging. Nucl Med (Stuttg). Jun. 30, 1975;14(2):163-171.

Vaupel, Hypoxia and Aggressive Tumor Phenotype: Implications for Therapy and Prognosis. Oncologist. 2008;13 Suppl 3:21-26.

Wiebe and McEwan, Scintigraphic Imaging of Focal Hypoxic Tissue: Development and Clinical Applications of 123I-IAZA. Brazilian Arch Biol Technol. Sep. 2002;45(special n):69-81.

Wiebe and Stypinski, Pharmacokinetics of SPECT radiopharmaceuticals for imaging hypoxic tissues. Q J Nucl Med. Sep. 1996;40(3):270-284.

Wiebe et al., Structure-Activity Relationships Among Nitroimidazole Nucleosides Used as Markers of Tissue Hypoxia. 7th Int Symp Radiopharmacol. Boston 1991.

Wiebe, PET radiopharmaceuticals for metabolic imaging in oncology. International Congress Series. 2004;1264:53-76.

\* cited by examiner

AZA Tosylate  F-MISO  FAZA

(A)

(B)

COMPOUNDS USEFUL IN IMAGING AND THERAPY

RELATED APPLICATIONS

The present invention is filed under 35 U.S.C. §371 as the United States national phase of International Application No. PCT/CA2011/000751, filed Jun. 27, 2011, which designated the United States and claims priority to U.S. application No. 61/358,163, filed on Jun. 24, 2010, the contents all of which are hereby incorporated by reference in their entirety.

FIELD OF THE INVENTION

The field of the invention generally relates to compositions and methods for synthesizing molecules and their use in theranostic (therapy+diagnostic) management of diseases manifesting focal hypoxia.

BACKGROUND OF THE INVENTION

Clinically useful molecular probes, including isotopically labeled probes, are an integral component of nuclear medicine, and offer a non-invasive approach to detecting disease, diagnosis, staging, restaging, and therapeutic management. Molecular probes using medical isotopes are used in a variety of disorder, including neurological and oncological diseases.

Positron- and Single Photon-Emitting Radiopharmaceuticals (PERs and SPERs) have evolved as preferred diagnostic tools since they contain short-lived radionuclides (e.g., T1/2, F-18=110 min; C-11=20 min), offering high image resolution and less radiation damage to the non-targeted body tissues because of the faster decay of the radioisotope.

The decay properties of the various radioisotopes of iodine offer trimodal (diagnosis, chemotherapy, and in situ in vivo molecular radiotherapy (MRT), e.g., by *IAZA [*I=$^{123/124/125/127/131}$I]) versatility to radioiodinated pharmaceuticals. No other element has isotopes suitable for SPECT/planar imaging ($^{123/131}$I), PET imaging ($^{124}$I) and radiotherapy (MRT; $^{124/125/131}$I). Using only one labeling element (i.e., iodine) also ensures that no metabolic or biochemical properties are modulated when moving from one modality to another. In brief, these radiopharmaceuticals can play a significant role in the theranostic (therapy+diagnostic) management of hypoxic diseases.

Such PER and SPER imaging systems create images based on the distribution of radiation-emitting radiopharmaceuticals in the body of a patient. The isotopes are typically administered to a patient by injection of probes (molecules) that comprise radiation-emitting radionuclides, such as F-18, C-11, N-13, O-15 or I-123, covalently attached to a molecule that is readily metabolized or localized in cells, or that chemically binds to macromolecules (i.e., receptors, enzymes) within cells. In some cases, the probe is administered to the patient as an ionic solution, metal chelate or by inhalation.

In some cancers, cell growth can develop in poorly vascularized, ischemic environments. Such environments that are removed from the vasculature or are poorly vascularized can become hypoxic, characterized by low tissue $pO_2$ levels.

Tissue hypoxia results from temporary or persistent ischemia (inadequate oxygen supply) (1). In tumors, hypoxia induces adaptive transcriptional and post-translational changes promoting the development of an aggressive phenotype which induces metastatic potential, promotes angiogenesis and supports local disease progression (1-5). Hypoxic tumors are clinically problematic as they can be resistant to both radiation therapy and/or cytotoxic therapy, which can result in treatment failure and poor outcomes. Therefore, assessing the level of tumor hypoxia may play a significant role in the outcome of the treatment and the therapy management of the cancer patients. Because hypoxic tumors respond poorly to both traditional radiation and cytotoxic therapies, identification of hypoxic tumors may indicate alternate approaches exist for treating hypoxic cancer cells.

Several techniques have been developed to measure the presence and extent of tumor hypoxia in vivo, ex vivo and in vitro. Determining tumor hypoxia via electrode measurements of $pO_2$ concentrations within the tumor is impractical in the clinical setting. The refinement of positron emission tomography (PET) techniques, with the advantage of short half-life positron-based radionuclides, and the development of hypoxia-specific positron emitting radiopharmaceuticals (PERs) have made PET a preferred non-invasive functional technique for clinical hypoxia imaging (7-9). Several PET and SPET nitroimidazole-based radiosensitizers (specifically, e.g., FAZA, IAZA) have been explored for scintigraphic imaging of hypoxia (10, 11); in the presence of low intracellular oxygen levels, they form adducts with hypoxic cellular macromolecules as the basis for their hypoxia-selective accumulation, and hence imaging properties. Nitroimidazole-based molecules demonstrate optimal reduction potentials for hypoxia-selective reductive binding that leads to their accumulation specifically and selectively in hypoxic tumor cells (12-17), and radioiodinated (*IAZA) and radiofluorinated ([$^{18}$F]-FAZA; [$^{18}$F]FAZA; $^{18}$F-FAZA $^{18}$FAZA) azomycin arabinosides are examples of 2-nitroimidazole (azomycin) nucleosides-based clinical radiopharmaceuticals that have gained extensive popularity for SPECT/PET-imaging and therapy management of hypoxic tissues.

Based on this hypoxia-selective retention, halogenated nucleoside derivatives of azomycin will selectively radiosensitize hypoxic cells to external beam x-ray radiotherapy (XRT), and when labeled with the appropriate radioiodine (*I) they will enable imaging-based discovery and assessment of hypoxic tissue ($^{123/124}$I) and delivery of therapeutic doses ($^{124/131}$I) of ionizing radiation to hypoxic tumors in situ in vivo (MRT); (3) Rapid clearance of these molecules from non-target tissues, an essential feature of drugs used for MRT (to reduce the radiation burden to non-target tissues) and radiosensitization (to reduce non-target dose-limiting toxicities), will reduce dose-limiting toxicities to the healthy tissues.

1-α-D-(5-deoxy-5-[*I]-iodoarabinofuranosyl)-2-nitroimidazole (*IAZA) and, 1-α-D-(5-deoxy-5-[$^{18}$F]-fluoroarabinofuranosyl)-2-nitroimidazole ($^{18}$FAZA), have been developed at the Cross Cancer Institute (CCI), Edmonton, Alberta, Canada (18) for their use in the diagnosis and potential therapy of hypoxic tumors (Kumar et al, 2005, Kumar et al 1998). $^{18}$FAZA is currently being used clinically in human cancer patients globally as a PET radiodiagnostic to assess the level of hypoxia in solid tumors and develop improved treatment plans (18-20). Preclinical studies have shown that $^{18}$FAZA, is rapidly cleared from the circulation and non-hypoxic tissues, and is excreted mainly via the renal pathway, thereby providing more favourable tumor-to-background ratios in most anatomical regions (21). In contrast, [$^{18}$F]-FMISO (22), a chemically-related but highly lipophilic clinical PET tracer in hypoxia management, is cleared primarily through the hepatobiliary route and undergoes non-specific lipoidal uptake in brain, liver and other organs, thereby interfering with the image quality in these regions of interest (23). Increasing clinical demands for $^{18}$FAZA (20, 24-27) requires the development of an improved and facile manufacturing process that could afford this product and other products of this class inexpensively and without much complication in the synthesis.

Typically, the synthesis of such probes requires a suitable precursor/synthon, and desirably an overall simple reaction quality of the radiolabeled mixture (e.g., minimal side products formation), short manufacture time, higher specific activity and/or the radiochemical yields since an inferior production process adversely affects the development.

It is therefore desirable to provide compositions and/methods for providing suitable precursors and/or methods for synthesizing such precursors. Such precursors can be incorporated into kits that are compatible with commercially available synthesis units, such as the GE Tracerlab etc., to produce PET radiotracers.

This background information is provided for the purpose of making known information believed by the applicant to be of possible relevance to the present invention. No admission is necessarily intended, nor should it be construed, that any of the preceding information constitutes prior art against the present invention.

SUMMARY OF THE INVENTION

In accordance with one aspect of the present invention there are provided a method for preparing 1-α-D-(5'-O-(4-nitrobenzenesulfonyl)-2',3'-di-O-acetyl-arabinofuranosyl)-2-nitroimidazole, comprising: reacting 2',3'-di-O-acetyl AZA with nosyl chloride to form a reaction mixture to give said 1-α-D-(5'-O-(4-nitrobenzenesulfonyl)-2',3'-di-O-acetyl-arabinofuranosyl)-2-nitroimidazole.

In accordance with another aspect of the present invention, there is provided a method for preparing 1-α-D-(5'-O-(4-nitrobenzenesulfonyl)-2',3'-di-O-acetyl-arabinofuranosyl)-2-nitroimidazole, comprising: reacting diacetyl IAZA with silver 4-nitrobenzenesulfonate to form a reaction mixture to give said -α-D-(5'-O-(4-nitrobenzenesulfonyl)-2',3'-di-O-acetyl-arabinofuranosyl)-2-nitroimidazole.

In accordance with another aspect of the present invention, there is provided a method for preparing 1-α-D-(5'-O-(4-nitrobenzenesulfonyl)-2',3'-di-O-acetyl-arabinofuranosyl)-2-nitroimidazole, comprising: reacting α-AZA with 4-nitrobenzenesulfonyl chloride to form a reaction mixture to give said -α-D-(5'-O-(4-nitrobenzenesulfonyl)-2',3'-di-O-acetyl-arabinofuranosyl)-2-nitroimidazole.

In accordance with another aspect of the present invention, there is provided a method for preparing 1-α-D-[5'-O-(4-nitrobenzenesulfonyl)-2',3'-di-O-trimethylacetylarabinofuranosyl]-2-nitroimidazole comprising: reacting 1-α-D-[5'-hydroxy-2',3'-di-O-trimethylacetylarabinofuranosyl]-2-nitroimidazole with 4-nitrobenzenesulfonyl chloride and DMAP to form a reaction mixture to give 1-α-D-[5'-O-(4-nitro benzene sulfonyl)-2',3'-di-O-trimethylacetylarabinofuranosyl]-2-nitroimidazole.

In accordance with another aspect of the present invention, there is provided a method for preparing 1-α-D-[5'-O-(4-nitrobenzenesulfonyl)-2',3'-di-O-trimethylacetylarabinofuranosyl]-2-nitroimidazole comprising: reacting 1-α-D-[5'-iodo-2',3'-di-O-trimethylacetylarabinofuranosyl]-2-nitroimidazole with silver 4-nitrobenzene sulfonate to form a reaction mixture to give 1-α-D-[5'-O-(4-nitrobenzenesulfonyl)-2',3'-di-O-trimethylacetylarabinofuranosyl]-2-nitroimidazole.

In accordance with another aspect of the present invention, there is a method for preparing 1-α-D-(5'-O-toluenesulfonyl-2,3-di-O-trimethylacetylarabinofuranosyl)-2-nitroimidazole comprising: reacting 1-α-D-[5'-hydroxyl-2',3'-di-O-trimethylacetylarabinofuranosyl]-2-nitroimidazole with toluenesulfonylchloride to form a reaction mixture to give 1-α-D-(5'-O-toluenesulfonyl-2,3-di-O-trimethylacetylarabinofuranosyl)-2-nitro imidazole.

In accordance with another aspect of the present invention, there is provided a method for preparing 1-α-D-(5'-O-toluenesulfonyl-2,3-di-O-trimethylacetylarabinofuranosyl)-2-nitroimidazole comprising: reacting 1-α-D-(5'-O-toluenesulfonylarabinofuranosyl)-2-nitroimidazole with trimethylacetyl (pivaloyl) chloride to form a reaction mixture to give 1-α-D-(5'-O-toluenesulfonyl-2,3-di-O-trimethylacetylarabinofuranosyl)-2-nitroimidazole.

In accordance with another aspect of the present invention, there if provided, a compound having the structure of formula I,

(I)

wherein: A is a monosaccharide, a homo-disaccharide, a hetero-disaccharide, a homo-heterotrisaccharide, heterotrisaccharide, or a polysaccharide; R is a substituted group or an unsubstituted group; and L is a leaving group.

In some aspects R is alkyl, alkenyl, aryl, heteroaryl, halogen, halo, —CF$_3$, nitro, amino, silylated amino, oxo, —OH, —OC(=O)C$_{1-5}$alkyl, —OC(=O)C$_{1-5}$aryl, —OC(=O)C$_{1-5}$aralkyl, —OCH$_2$C(=O)C$_{1-5}$alkyl, —OCH$_2$C(=O)C$_{1-5}$aryl, —OCH$_2$C(=O)C$_{1-5}$aralkyl, —OCH$_2$OC$_{1-5}$ alkyl, —OSiR$_3$, —OCH$_2$OC$_{1-5}$alkyl, carboxyl, silylated carboxyl, —COOC$_{1-5}$alkyl, —OC$_{1-5}$alkyl, —CONHC$_{1-5}$alkyl, —NH-COC$_{1-5}$alkyl, —OSOC$_{1-5}$alkyl, —SOOC$_{1-5}$alkyl, —SOONHC$_{1-5}$ alkyl, —NHSO$_2$C$_{1-5}$alkyl, or —CH$_2$—(CH$_2$)$_n$—OSiR$_3$, each of which may be further substituted and wherein n=0-6.

In other aspects, R is —OH, —NH$_2$, —SH, —BH$_2$, —F, or —O-acetyl, —O-pivaloyl, —O-allyl, —O-allyloxycarbonyl, —O-benzyl, —O-benzyl, —O-benzyloxycarbonyl, —O-benzyloxymethyl, —O-tert-butoxycarbonyl, —O-tert-butyl, —O-tert-butyldimethylsilyl, —O-tert-butyldiphenylsilyl, —O-tert-butylmethylsilyl, —O-chloroacetyl, —O-diethylisopropylsilyl, —O-3,4-dimethoxybenzyl, —O-levulinoyl, —O-methylacetyl, —O-4-methoxybenzyl, —O-4-methoxybenzyloxymethyl, —O-2-methoxymethyl, —O-2-methoxyethoxymethyl, —O-methylthiomethyl, —O-4-nitrobenzyloxycarbonyl, —O-tetrahydropyran-2-yl, —O-thexyldimethylsilyl, —O-2,2,2-trichloro ethoxycarbonyl, —O-triethylsilyl, —O-triisopropylsilyl, —O-trimethylsilyl, —O-2-(trimethylsilyl)ethoxycarbonyl, —O-3-(trimethylsilyl)ethoxymethyl, —O-triphenylsilyl, or —O-trityl.

In some aspects said leaving group L is halogen, alkylsulfonyloxy, perfluoroalkylsulfonyloxy, arylsulfonyloxy, substituted alkylsulfonyloxy, substituted arylsulfonyloxy, a substituted organometallic leaving group, a substituted mercury-based leaving group, substituted silyl, any moiety replaceable by halogen, radiohalogen, nucleophile or electrophile.

In some aspects said leaving group is joined to said A directly or via an intermediate moiety that is connected to A.

In some aspects A is of the formula:

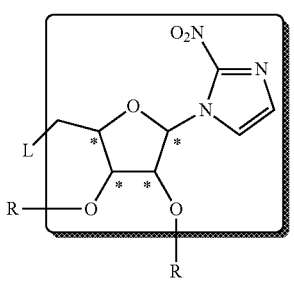

wherein the chiral centers may be (R) or (S) configuration; L is halogen, alkylsulfonyloxy, perfluoroalkylsulfonyloxy, arylsulfonyloxy, substituted alkylsulfonyloxy, or substituted arylsulfonyloxy; and R is H or —C(=O)R$^1$, wherein R$^1$ is alkyl, aryl, aralkyl, heteroaryl, heterocyclic —CH$_2$C(C=O)C$_{1-5}$alkyl, —CH$_2$C(=O)C$_{1-5}$aryl, —CH$_2$C(=O)C$_{1-5}$aralkyl, —CH$_2$OC$_{1-5}$alkyl, —SiR$_3$, —CH2OC$_{1-5}$alkyl, —CH$_2$—(CH$_2$)$_n$—SiR$_3$, or —CH$_2$—(CH$_2$)$_n$—OSiR$_3$ and n is 0-6.

In some aspects, R is H, -acetyl, -pivaloyl, -allyl, -allyloxycarbonyl, -benzyl, -benzyl, -benzyloxycarbonyl, -benzyloxymethyl, -tert-butoxycarbonyl, -tert-butyl, -tert-butyldimethylsilyl, -tert-butyldiphenylsilyl, -tert-butylmethylsilyl, -chloroacetyl, -diethylisopropylsilyl, -3,4-dimethoxybenzyl, -levulinoyl, -methylacetyl, -4-methoxybenzyl, -4-methoxybenzyloxymethyl, -2-methoxymethyl, -2-methoxyethoxymethyl, -methylthiomethyl, -4-nitrobenzyloxycarbonyl, -tetrahydropyran-2-yl, -thexyldimethylsilyl, -2,2,2-trichloroethoxycarbonyl, -triethylsilyl, -triisopropylsilyl, -trimethylsilyl, -2-(trimethylsilyl)ethoxycarbonyl, -3-(trimethylsilyl)ethoxymethyl, -triphenylsilyl or -trityl.

In some aspects said compound is of the formula

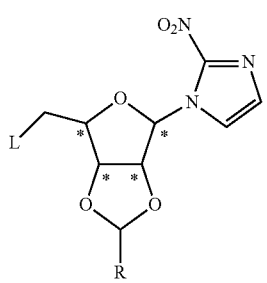

wherein the chiral centers may be (R) or (S) configuration; L is halogen, alkylsulfonyloxy, perfluoroalkylsulfonyloxy, arylsulfonyloxy, substituted alkylsulfonyloxy or substituted arylsulfonyloxy; and R is 1-1, alkyl, aryl, aralkyl, heteroaryl, heterocyclic.

In some aspects, said compound is of the formula

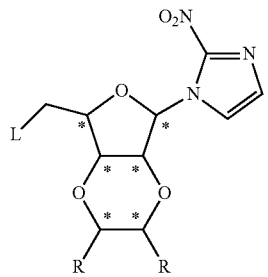

wherein the chiral centers may be (R) or (S) configuration; L is halogen, alkylsulfonyloxy, perfluoroalkylsulfonyloxy, arylsulfonyloxy, substituted alkylsulfonyloxy, or substituted arylsulfonyloxy; and R is H, alkyl, aryl, aralkyl, heteroaryl, or heterocyclic.

In some aspect said compound is 1-α-D-(5'-O-(4-nitrobenzenesulfonyl)-2',3'-di-O-acetyl-arabinofuranosyl)-2-nitroimidazole; 1-α-D-[5'-O-(4-nitrobenzenesulfonyl)-2',3'-di-O-trimethylacetylarabinofuranosyl]-2-nitroimidazole; or 1-α-D-(5'-O-toluenesulfonyl-2,3-di-O-trimethylacetylarabinofuranosyl)-2-nitroimidazole.

In one aspect of the present invention, said compound is 1-α-D-(5'-O-(4-nitrobenzenesulfonyl)-2',3'-di-O-acetyl-arabinofuranosyl)-2-nitroimidazole.

In one aspect of the present invention, said compound is 1-α-D-[5'-O-(4-nitrobenzenesulfonyl)-2',3'-di-O-trimethylacetylarabinofuranosyl]-2-nitroimidazole.

In one aspect of the present invention, said compound is 1-α-D-(5'-O-toluenesulfonyl-2,3-di-O-trimethylacetylarabinofuranosyl)-2-nitro imidazole.

In another aspect of the present invention, there is provided a use of a compound or salt as described herein, in the manufacture of an imaging, chemotherapy or radiotherapy agent.

In another aspect of the present invention, there is provided a kit for the manufacture of an imaging, chemotherapy or radiotherapy agent, comprising: a compound as described herein; and instructions for the use thereof.

BRIEF DESCRIPTION OF THE DRAWINGS

Embodiments of the present invention will now be described, by way of example only, with reference to the attached Figures, wherein.

DETAILED DESCRIPTION

Figure 1:
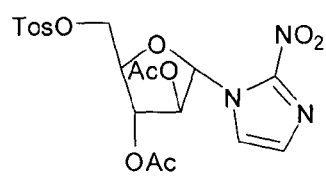
FIG. 1 depicts the structures of diacetyl AZA tosylate, current $^{18}$F-FAZA precursor, F-MISO and FAZA.
Figure 1:
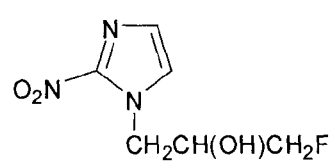
Figure 1:
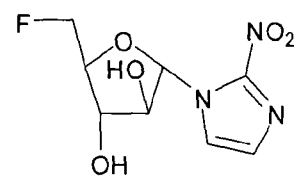

The present invention relates to the development of novel chemical precursors/synthons, and their chemical and radiochemical derivatives and methods. For example, derivatization with a radionuclide is used to synthesize and manufacture radiopharmaceuticals for use as radiodiagnostic, radiotherapeutic, radiochemotherapeutic and chemotherapeutic agents.

In one embodiment, the present application describes the synthesis and development of novel precursors/synthons for synthesizing isotopically (radio)labeled sugars- and sugar-coupled molecules, and their chemical modifications.

The radiolabeled products can be obtained by using a fully automated procedure that, after optimization of reaction parameters for the targeted molecule, can be adapted for use in automated manufacturing units.

In another aspect of the present invention, the compositions and methods are suited for use in a cartridge device or micro reactor device, comprising one or more microfluidic channels or tubes (also referred to as microchannels or capillaries) having at least one cross-sectional dimension (e.g., height, width, depth, diameter) suited for micro volumes. The microchannels make it possible to manipulate small volumes of liquid on.

In one embodiment, the application describes a general scheme represented as:

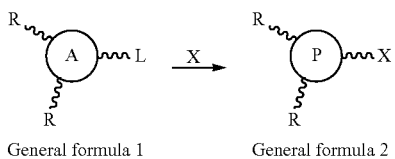

General formula 1    General formula 2

Wherein: X is a halogen, radiohalogen, nucleophile or electrophile.

L is a leaving group joined to the molecule directly or via an intermediate moiety (linker) that is connected to the moiety.

The term "leaving group" as used herein, refers to groups that are readily displaced, for example, by a nucleophile. Such leaving groups are well known. Non-limiting examples of 'L' include a halogen, alkyl/arylsulfonyloxy, substituted alkyl/arylsulfonyloxy etc., substituted organometallic leaving groups e.g., stannyl, substituted mercury-based leaving groups but not limited to these, substituted silyl or any moiety replaceable by the halogen, radiohalogen, nucleophile or electrophile, joined to the molecule directly or via an intermediate moiety (i.e., linker) that is connected to the moiety.

The term "linker" as used herein, refers to a chain substituted or unsubstituted, comprising, for example, 1 to 10 atoms and may comprise, for example, 1, 2 or 3 adjacent or non-adjacent atoms or groups. The linker may also comprise part of a saturated, unsaturated, aralkyl or aromatic ring that may be unsubstituted or further substituted.

R is a substituted or unsubstituted group.

The terms "substituted" or "substituent" as used herein, refer to a compound, moiety, or functional group comprising one or more hydrogen atom of which is substituted by a group (a substituent) such as a —$C_{1-5}$alkyl, $C_{2-5}$alkenyl, halogen or halo (chlorine, fluorine, bromine, iodine atom), —$CF_3$, nitro, amino (—$NH_2$, —NHR, —$NR_2$, etc. . . . ), silylated amino (—NH—Si—$R_2$, —N—[$SiR_2$]$_2$, where R may be same or different), oxo (i.e., forming —C(=O)—), —OH, silylated —OH(—O—Si—$R_3$ where R may be same or different), carboxyl (—COOH), silylated carboxyl (—COO—$SiR_2$, where R may be same or different), —COO$C_{1-5}$alkyl, —O$C_{1-5}$ alkyl, —CONH$C_{1-5}$alkyl, —NHCO$C_{1-5}$alkyl, —OSO$C_{1-5}$alkyl, —SO OC$_{1-5}$alkyl, —SOONH$C_{1-5}$alkyl, —NHSO$_2C_{1-5}$alkyl, aryl, heteroaryl and the like, each of which may be further substituted.

The term "alkyl, as used herein, refers to a hydrocarbon chain, typically ranging from about 1 to 20 atoms in length. Such hydrocarbon chains may be branched or straight chain, substituted or unsubstituted.

The term "aryl" as used herein, refers to one or more aromatic rings. Aryl includes multiple aryl rings that may be fused, as in naphthyl or unfused, as in biphenyl. Aryl rings may also be fused or unfused with one or more cyclic hydrocarbon, heteroaryl, or heterocyclic rings.

The term "aralkyl" as used herein, refers to one or more alkyl substituted aromatic rings. Alkyl chains may be further substituted or unsubstituted. Aryl includes multiple aryl rings that may be fused, as in naphthyl or unfused, as in biphenyl. Aryl rings may also be fused or unfused with one or more cyclic hydrocarbon, heteroaryl, or heterocyclic rings.

The term "heteroaryl" as used herein, is an aryl group containing from one to four heteroatoms, preferably N, O, or S, or a combination thereof. Heteroaryl rings may also be fused with one or more cyclic hydrocarbon, heterocyclic, aryl, or heteroaryl rings.

The term "alkenyl" as used herein, refers to a monovalent, unbranched or branched hydrocarbon chain having one or more double bonds. The double bond of an alkenyl group can be unconjugated or conjugated to another unsaturated group.

In one example, R is —OH, —$NH_2$, —SH, —$BH_2$, F or combinations thereof, on precursor molecule A.

When A contains more than one R, one of the R's can be substituted with or without a linker to a homo or heteroaromatic moiety. The anomeric bond may be a/P. All configurations of the sugar moiety are contemplated.

A denotes a monosaccharide, a homo- or hetero-disaccharide, a homo- or heterotrisaccharide or a polysaccharide.

P=A, but represent the corresponding product core that is formed after the precursor's reaction with X.

In some examples, R is alkyl, alkenyl, aryl, heteroaryl, halogen, halo, —$CF_3$, nitro, amino, silylated amino, oxo, —OH, —OC(=O)$C_{1-5}$alkyl, —OC(=O)$C_{1-5}$aryl, —OC(=O)$C_{1-5}$aralkyl, —OCH$_2$C(C=O)$C_{1-5}$alkyl, —OCH$_2$C(=O)$C_{1-5}$aryl, —OCH$_2$C(=O)$C_{1-5}$aralkyl, —OCH$_2$OC$_{1-5}$alkyl, —OSiR$_3$, —OCH$_2$OC$_{1-5}$alkyl, carboxyl, silylated carboxyl, —COO$C_{1-5}$alkyl, —O$C_{1-5}$alkyl, —CONH$C_{1-5}$alkyl, —NHCO$C_{1-5}$alkyl, —OSO$C_{1-5}$alkyl, —SOO$C_{1-5}$alkyl, —SOONH$C_{1-5}$alkyl, —NHSO$_2C_{1-5}$alkyl, or —CH$_2$—(CH$_2$)$_n$—OSiR$_3$, each of which may be further substituted and wherein n=0-6.

In some examples, R is —OH, —$NH_2$, —SH, —$BH_2$, —F, or —O-acetyl, —O-pivaloyl, —O-allyl, —O-allyloxycarbonyl, —O-benzyl, —O-benzyl, —O-benzyloxycarbonyl, —O-benzyloxymethyl, —O-tert-butoxycarbonyl, —O-tert-butyl, —O-tert-butyldimethylsilyl, —O-tert-butyldiphenyl silyl, —O-tert-butylmethylsilyl, —O-chloroacetyl, —O-diethylisopropylsilyl, —O-3,4-dimethoxybenzyl, —O-levulinoyl, —O-methylacetyl, —O-4-methoxybenzyl, —O-4-methoxybenzyloxymethyl, —O-2-methoxymethyl, —O-2-methoxyethoxymethyl, —O-methylthiomethyl, —O-4-nitrobenzyloxycarbonyl, —O-tetrahydropyran-2-yl, —O-thexyldimethylsilyl, —O-2,2,2-trichloroethoxycarbonyl, —O-triethylsilyl, —O-triisopropylsilyl, —O-trimethylsilyl, —O-2-(trimethylsilyl)ethoxycarbonyl, —O-3-(trimethylsilyl)ethoxymethyl, —O-triphenylsilyl, or —O-trityl.

In some examples said leaving group L is halogen, alkylsulfonyloxy, perfluoroalkylsulfonyloxy, arylsulfonyloxy, substituted alkylsulfonyloxy, substituted arylsulfonyloxy, a substituted organometallic leaving group, a substituted mercury-based leaving group, substituted silyl, any moiety replaceable by halogen, radiohalogen, nucleophile or electrophile.

In some examples leaving group is joined to said A directly or via an intermediate moiety that is connected to A.

In one example, A is of the formula:

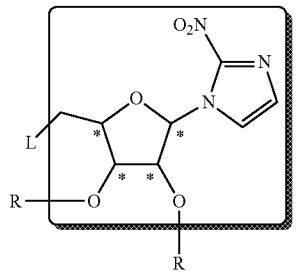

wherein the chiral centers may be (R) or (S) configuration; L is halogen, alkylsulfonyloxy, perfluoroalkylsulfonyloxy, arylsulfonyloxy, substituted alkylsulfonyloxy, or substituted arylsulfonyloxy; and R is H or —C(=O)R$^1$, wherein R$^1$ is alkyl, aryl, aralkyl, heteroaryl, heterocyclic —CH$_2$C(C=O)C$_{1-5}$alkyl, —CH$_2$C(=O)C$_{1-5}$aryl, —CH$_2$C(=O)C$_{1-5}$aralkyl, —CH$_2$OC$_{1-5}$alkyl, —SiR$_3$, —CH$_2$OC$_{1-5}$alkyl, —CH$_2$—(CH$_2$)$_n$—SiR$_3$, or —CH$_2$—(CH$_2$)$_n$—OSiR$_3$ and n is 0-6.

In one example, R is H, -acetyl, -pivaloyl, -allyl, -allyloxycarbonyl, -benzyl, -benzyl, -benzyloxycarbonyl, -benzyloxymethyl, -tert-butoxycarbonyl, -tert-butyl, -tert-butyldimethylsilyl, -tert-butyldiphenylsilyl, -tert-butylmethylsilyl, -chloroacetyl, -diethylisopropylsilyl, -3,4-dimethoxybenzyl, -levulinoyl, -methylacetyl, -4-methoxybenzyl, -4-methoxybenzyloxymethyl, -2-methoxymethyl, -2-methoxyethoxymethyl, -methylthiomethyl, -4-nitrobenzyloxycarbonyl, -tetrahydropyran-2-yl, -thexyldimethylsilyl, -2,2,2-trichloroethoxycarbonyl, -triethylsilyl, -triisopropylsilyl, -trimethylsilyl, -2-(trimethylsilyl)ethoxycarbonyl, -3-(trimethylsilyl)ethoxymethyl, -triphenylsilyl or -trityl.

In one example said compound is of the formula

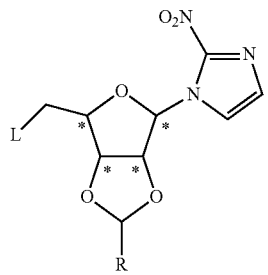

wherein the chiral centers may be (R) or (S) configuration; L is halogen, alkylsulfonyloxy, perfluoroalkylsulfonyloxy, arylsulfonyloxy, substituted alkylsulfonyloxy or substituted arylsulfonyloxy; and R is H, alkyl, aryl, aralkyl, heteroaryl, heterocyclic.

In one example, said compound is of the formula

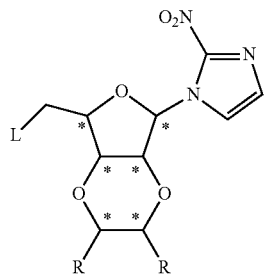

wherein the chiral centers may be (R) or (S) configuration; L is halogen, alkylsulfonyloxy, perfluoroalkylsulfonyloxy, arylsulfonyloxy, substituted alkylsulfonyloxy, or substituted arylsulfonyloxy; and R is H, alkyl, aryl, aralkyl, heteroaryl, or heterocyclic.

In another example, the application described the scheme as follows:

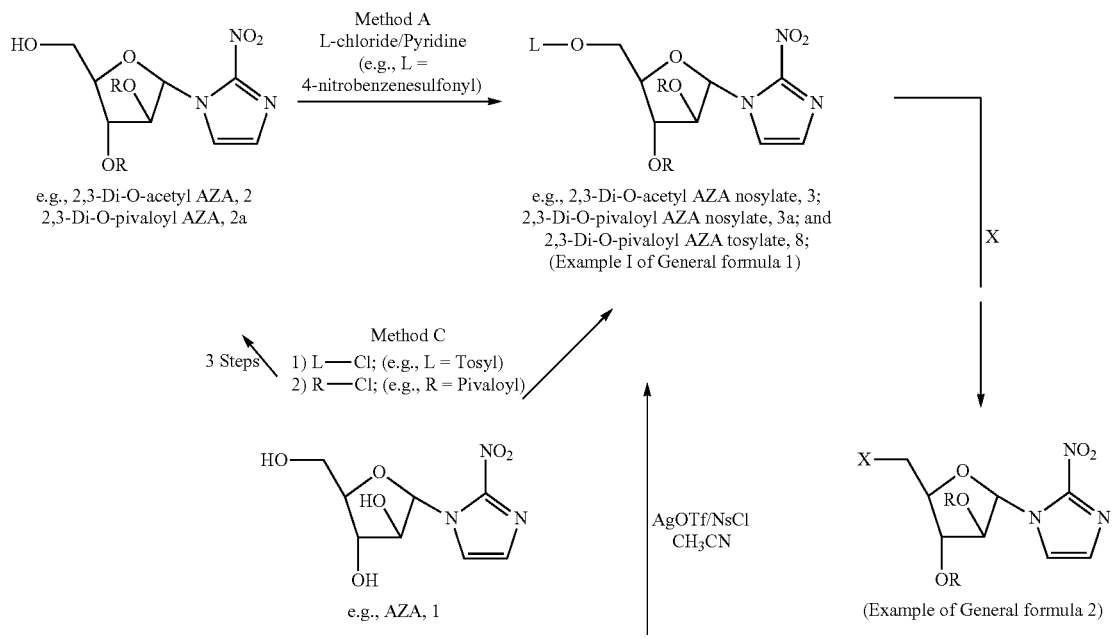

-continued

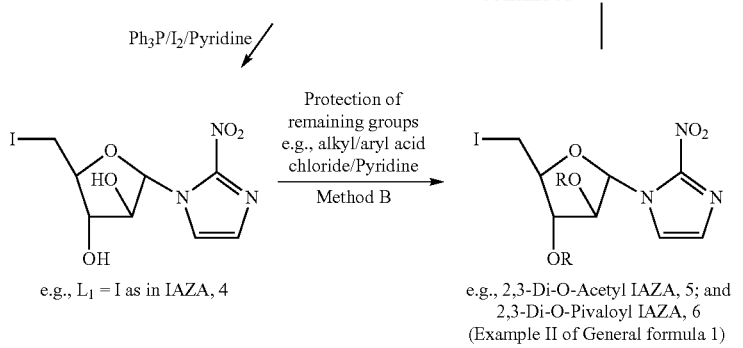

e.g., L₁ = I as in IAZA, 4 e.g., 2,3-Di-O-Acetyl IAZA, 5; and
2,3-Di-O-Pivaloyl IAZA, 6
(Example II of General formula 1)

Typically, radiopharmaceutical products comprise two functional components, one being radioactive and the other not being radioactive. The radioactive component makes possible the detection of the product in the context of the theranosis (diagnosis+therapy) and it constitutes the active agent in the case of therapeutic use. It is a radionuclide with appropriate physical properties. The nonradioactive component, for its part, is a molecule or tracer, intended to accumulate in the target organ, tissue, tumor and/or site, and the like, to ensure the accumulation of radioactivity.

In one aspect of the present invention, there is provided precursors/synthons useful for the production of molecules (such as radiochemical compounds) for imaging, detection, diagnosis, chemotherapy, radiochemotherapy, and molecular radiotherapy (MRT) of disease in a subject. In one example, the radiolabelled compounds are useful for detecting hypoxic conditions present in, e.g., tissues of the brain, head and neck, lungs, heart, eyes, kidney, liver, pancreas, thymus, intestines, urogenital organs, stomach, skin, and bone. The hypoxic conditions can result from ischemia (e.g., as a result of stroke), inflammation, wound healing, and cancer. In another example, the radiolabelled compounds will contain a therapeutic radionuclide (e.g., $^{131/124/125}$I) which will provide self-sensitizing low doses of the radiation to kill the tumor cells. These compounds will be useful for molecular radiotherapy (MRT) of hypoxic tumors.

The term "radiochemical" as used herein includes any organic, inorganic or organometallic compound comprising a covalently-attached radioactive diagnostic or therapeutic isotope, any coordinated radioactive ligand or isotope for diagnosis and therapy, any inorganic radioactive ionic solution, any superparamagnetic naonparticle-linked (substituted or linked) molecule-attached with radioactive diagnostic or therapeutic molecule, or any radioactive gas, including radioactive molecular imaging probes intended for administration to a patient (e.g., by inhalation, ingestion or intravenous injection) for tissue imaging and/or radiotherapy purposes for killing the hypoxic tumor cells, which are also referred to in the art as radiopharmaceuticals, radiotracers, radioligands or radiotherapeutics.

The term "radioactive isotope" or "radioactive element" as used herein, refers to isotopes undergoing radioactive decay (e.g., emitting radiation) and radiolabeling agents comprising a radioactive isotope. Such isotopes or elements are also referred to in the art as radioisotopes or radionuclides.

The precursors of the present invention contain nucleophilically substitutable moieties that can be chemically reacted to incorporate a variety of short-lived radionuclides such as radiohalogens, e.g. F-18, radioiodines (I-123/124/125/131), carbon-11, and long lived radioisotopes e.g., H-3, C-14 and S-35 etc. The synthesis process for the class of the molecules (containing naturally abundant isotopes or corresponding radioisotopes) described herein may involve a conventional thermal chemistry process or a non-conventional process e.g. using microwave (MW) chemistry or a microfluidic process, but not limited to these synthesis techniques. The processes of the present application can also be adapted to develop processor-controlled automated synthesis processes where sequential release of the reagents to the reactor, reaction parameters e.g., temperature, duration, amounts of various reagents, and the purification process will be controlled by a software, or combination of software.

In one example of the present invention, one class of the compounds (2-nitroimidazole based sugar-coupled molecules) was evaluated, and was found to provide superior (radio)chemical yields, fewer secondary products, and a cleaner radiolabeling profile in comparison to the existing precursors.

The radiochemicals produced using the compositions and methods of the present application are suitable for use in a number of diseases, including but not limited to, oncological disorders, diabetes, inflammatory disorders and stroke.

Methods of the present invention are conveniently practiced by providing the compound(s) and/or composition(s) used in such method in the form of a kit. Such a kit preferably contains the instructions of the use thereof.

In one example, there is provided a kit for the manufacture of an imaging agent, comprising: a compound as described herein; and instructions for the use thereof.

In one example, the kit further comprises a radionuclide.

In one example, said imaging, chemotherapy or radiotherapy agent is FAZA or IAZA.

In one example, said imaging agent, chemotherapy or radiotherapy is suitable for manufacture using an automated radio-synthesis unit.

EXAMPLES

Methods
Chemistry.

All chemicals used were, purchased from Sigma-Aldrich Co., USA, were reagent grade, and used without any further purification. Solvents were dried over appropriate drying agents and freshly distilled before use. The progress of synthetic reactions was monitored by thin layer chromatography (tlc; 90:10, v/v, solvent system B) or hexanes:EtOAc (7:1, v/v, solvent system C; 3:2, v/v, solvent system D and 1:1, v/v, solvent system E) as developing solvents. Column chromatography was performed on Merck silica gel 60 (particle size 70-200 and 230-400 mesh ASTM). Melting points were determined on a Büchi capillary melting point apparatus and are uncorrected. $^1$H and $^{13}$C NMR spectra were recorded on a Bruker AM-300 spectrometer in deuterated chloroform (CDCl$_3$) or deuterated methanol (CD$_3$OD), depending on the solubility of the product. Chemical shifts are reported in ppm downfield with respect to tetramethylsilane as an internal standard. The $^1$H NMR assignments were confirmed by selective decoupling experiments. The $^{13}$C NMR resonances are assigned by using the J modulation spin echo technique to determine the number of hydrogen atoms attached to each carbon atom. The protons and carbons of the sugar moiety and nitroimidazole are represented by a single prime (') and no prime, respectively. When necessary, high resolution mass spectra (HRMS) were recorded using an AEI-MS-12 mass spectrometer.

TR19 negative ion accelerating cyclotron capable of accelerating protons to 19 MeV and deuterons to 9.5 MeV (Advanced Cyclotron Systems, Inc.) with an external high performance multicusp ion source greater than 150 μA beam current with dual simultaneous beam extraction was used for $^{18}$F production. The radiofluoride target consisting of a niobium body with HAVAR foil window was used for production of $^{18}$F via $^{18}$O(p,n)$^{18}$F reaction by irradiating highly $^{18}$O enriched water (H$_2^{18}$O). Tracerlab FX automated synthesis units (ASU) employed for the manufacture of $^{18}$F-FAZA was purchased from G.E. Medical Technologies Inc., Canada which operates on the basis of performing unit operations under computer (CPU) control, involving the movement of liquids, movement of gases (vacuum, pressure), valve actuation and heating systems on a time dependent basis through a well defined flow path. Feedback control, monitoring and diagnostic functions are built into the operation using various sensor-based systems.

Example I of General Formula 1

1-α-D-(5'-O-(4-nitrobenzenesulfonyl)-2',3'-di-O-acetyl-arabinofuranosyl)-2-nitroimidazole (Diacetyl AZA nosylate, 3), 1-α-D-(5'-O-(4-nitrobenzenesulfonyl)-2',3'-di-O-pivaloyl-arabinofuranosyl)-2-nitroimidazole (Dipivaloyl AZA nosylate, 3a), 1-α-D-(5'-O-(toluenesulfonyl)-2',3'-di-O-pivaloyl-arabinofuranosyl)-2-nitroimidazole (Dipivaloyl AZA tosylate, 8), and their Precursors were Synthesized Under the General Formula 1

Example 1

1-α-D-(5'-O-(4-nitrobenzenesulfonyl)-2',3'-di-O-acetyl-arabinofuranosyl)-2-nitroimidazole (Diacetyl AZA nosylate, DiAc Ns-AZA, Acetyl Ns AZA; 3)

This compound was synthesized by three methods A, B and C.

Method A for Diacetyl AZA Nosylate, 3:

Nosyl chloride (0.674 g, 3.04 mmol) was added to a stirred pre-cooled solution of 2',3'-di-O-acetyl AZA, 2, (0.5 g, 1.52 mmol) in anhydrous pyridine (8 ml) at 0° C. under an atmosphere of argon. The stirring was continued for 3 h at this temperature, and then for an additional 1 h at 22° C. The progress of the reaction was quenched by adding a piece of ice, the solvents were evaporated under reduced pressure and the crude product was dissolved in ethyl acetate (5 ml) and washed with water (3×5 ml). The organic layer was dried (MgSO$_4$) and evaporated under reduced pressure to give 0.75 g of impure product. The crude material was purified by flash silica gel column chromatography (hexanes:EtOAc; 1:2; v/v) to give pure diacetyl AZA nosylate, Compound 3, as white foam. In addition, this reaction also afforded 5'-chloro-5'-deoxy-2',3'-di-O-acetyl AZA, as white foam which was recrystallized from ether/hexane (5 mL, 1:1, v/v) to give white crystals. The characterization data for these compounds are provided below.

Diacetyl AZA nosylate, 3:

Yield 0.23 g (29%); thermal softening, 49-51° C.; Rf 0.63 (5% MeOH in CHCl$_3$); $^1$H NMR (CDCl$_3$): 2.02 and 2.22 (two s, each for 3H, two acetyl)), 4.37 and 4.43 (two dd, J$_{5',4'}$=2.4 Hz, J$_{5'',4'}$=4.6 Hz, and J$_{gem}$=12.8 Hz, 2H, H-5' and H-5''), 4.54 (ddd, J$_{3',4'}$=J$_{5',4'}$=2.4 Hz, J$_{5'',4'}$=4.6 Hz 1H, H-4'), 5.13 (d, J$_{3',2'}$=1.8 Hz, 1H, H-3'), 5.45 (s, 1H, H-2'), 6.61 (s, 1H, H-1'), 7.22 (s, 1H, imidazole H-4), 7.29 (s, 1H, imidazole H-5), 8.17 (dd, J$_{2,3}$=J$_{6,5}$=8.8 Hz, J$_{5,3}$=J$_{6,2}$=1.8 Hz, 2H, H-3 and H-5 of phenyl), and 8.44 (dd, J$_{3,2}$=J$_{5,6}$=8.9 Hz, J$_{3,5}$=J$_{2,6}$=1.8 Hz, 2H, H-2 and H-6 of phenyl) ppm; $^{13}$C NMR (CDCl$_3$) δ 20.27 (2×CH$_3$), 68.56 (C-5'), 76.21 (C-4'), 80.81 (C-3'), 84.75 (C-2'), 92.91 (C-1'), 121.77 (imidazole C-4), 124.52 (phenyl C-3 and C-5), 128.54 (imidazole C-5), 129.30 (phenyl C-2 and C-6), 141.02 (phenyl C-4), 143.91 (imidazole C—NO$_2$), 150.95 (phenyl C-1), 168.68 (C═O at C-2'), 169.28 (C═O at C-3') ppm; Analysis for C$_{18}$H$_{18}$N$_4$O$_{12}$S Calc. C, 42.03; H, 3.53; N, 10.89. Found C, 42.16; H, 3.58; N, 10.47; HRMS (EI) for C$_{18}$H$_{18}$N$_4$O$_{12}$SNa Calc. 537.05341; found 537.05329 (M$^+$ 94.18%); Analysis for C$_{18}$H$_{18}$N$_4$O$_{12}$S Calc. C, 41.45; H, 4.06; N, 12.08. Found C, 42.03; H, 3.53; N, 10.89; HRMS (EI)—C$_{18}$H$_{18}$N$_4$O$_{12}$S. Calc. 514.42; Found 514.06.

5'-Chloro-5'-deoxy-2',3'-di-O-acetyl AZA

Yield 0.29 g (55%); mp 129-131° C.; Rf 0.71 (5% MeOH in CHCl$_3$); $^1$H NMR (CDCl$_3$): 2.02 and 2.22 (two s, each for 3H, two acetyl)), 4.37 and 4.43 (two dd, J$_{5',4'}$=2.4 Hz, J$_{5'',4'}$=4.8 Hz, and J$_{gem}$=12.8 Hz, 2H, H-5' and H-5'') 4.54 (ddd, J$_{3',4'}$=J$_{5',4'}$=2.4 Hz, J$_{5'',4'}$=4.8 Hz 1H, H-4'), 5.13 (d, J$_{3',2'}$=1.8 Hz, 1H, H-3'), 5.45 (s, 1H, H-2'), 6.61 (d, J$_{2',1'}$=1.2 Hz, 1H, H-1'), 7.22 (s, 1H, imidazole H-4), 7.29 (s, 1H, imidazole H-5), 8.17 (dd, J$_{2,3}$=J$_{6,5}$=6.7 Hz, J$_{5,3}$=J$_{6,2}$=1.8 Hz, 2H, H-3 and H-5 of phenyl), and 8.44 (dd, J$_{3,2}$=J$_{5,6}$=6.7 Hz, J$_{3,5}$=J$_{2,6}$=1.8 Hz, 2H, H-2 and H-6 of phenyl) ppm; $^{13}$C NMR (CDCl$_3$) δ 20.46 and 20.51 (two CH$_3$), 38.77 (carbon of tert-butyl at C-3'), 68.52 (C-5'), 76.17 (C-4'), 80.80 (C-3'), 84.85 (C-2'), 93.01 (C-1'), 121.81 (imidazole C-4), 124.55 (phenyl C-3 and C-5), 128.53 (imidazole C-5), 129.35 (phenyl C-2 and C-6), 140.98 (phenyl C-4), 143.91 (imidazole C—NO$_2$), 150.95 (phenyl C-1), 168.76 (C═O at C-2'), 169.35 (C═O at C-3') ppm; Analysis for C$_{12}$H$_{14}$ClN$_3$O$_7$ Calc. C, 41.45; H, 4.06; N, 12.08; Cl, 10.20. Found C, 41.73; H, 3.84; N, 11.90; Cl, 10.16.

5'-Chloro-5'-deoxy AZA

A solution of 5'-Chloro-5'-deoxy-AZA (0.20 g, 0.575 mmol) in methanolic ammonia (2M, 5 mL) was stirred at 22° C. for 16 h and then the solvent was evaporated under reduced pressure using a rotary evaporator. The residue was purified by a flash silica gel column chromatography using 5% MeOH in CH$_2$Cl$_2$ as an eluent. The process afforded a colorless oil which was recrystallized from ether/hexane (2:1, 15 mL) to give white crystals. Yield 0.15 g (96%); mp 133-135° C.; Rf 0.29 (5% MeOH in CH$_2$Cl$_2$); $^1$H NMR (CDCl$_3$): 3.75 (dd, J$_{5',4'}$=6.6 Hz, J$_{gem}$=14.2 Hz, 1H, H-5'), 3.80 (dd, J$_{5'',4'}$=7.3 Hz, J$_{gem}$=13.2 Hz, 1H, H-5''), 4.19 (d, J$_{4',3'}$=1.1 Hz, 1H, H-3'), 4.28 (s, 1H, H-2'), 4.60 (ddd, J$_{3',4'}$=1.1 Hz, J$_{5',4'}$=6.6 Hz, $J_{5'',4'}$=7.3 Hz 1H, H-4'); 6.45 (s, 1H, H-1'), 7.12 (s, 1H, imidazole H-4), 7.65 (s, 1H, imidazole H-5) ppm; $^{13}$C NMR (CD$_3$OD) δ 44.63 (C-5'), 78.51 (C-4'), 83.65 (C-3'), 90.93 (C-2'), 97.25 (C-1'), 125.26 (imidazole C-4), 128.04 (imidazole C-5), 145.19 (imidazole C—NO$_2$) ppm; Analysis for C$_8$H$_{10}$ClN$_3$O$_5$ (263.63) Calc. C, 36.45; H, 3.82; N, 15.94; Cl, 13.45. Found C, 36.70; H, 3.77; N, 15.54, Cl, 13.37.

Method B for Diacetyl AZA nosylate, 3:

Silver 4-nitrobenzenesulfonate (186 mg, 0.6 mmol) was dissolved in anhydrous acetonitrile (1 mL) and the mixture was added to diacetyl IAZA (88 mg, 0.2 mmol) in a capped vial and stirred vigorously at 60° C. for 4 hours. The tlc analysis of the reaction mixture at this time showed the exhaustion of diacetyl IAZA and the formation of 3. The reaction mixture was filtered and the solvent was evaporated under reduced pressure. The residue, so obtained, was purified by flash silica gel column chromatography using EtOAc/toluene (1:1; v/v) as an eluent to afford 3 as a foam 42 mg. (yield 40%). Proton and carbon NMR data for 3, obtained using method B were same as those obtained by method A.

Method C for Diacetyl AZA nosylate, 3:

4-nitrobenzenesulfonyl (nosyl) chloride (135 mg, 0.6 mmol) in pyridine (0.5 ml) was added to a stirred solution of α-AZA, 1, (150 mg, 0.62 mmol) in pyridine (2 ml) at −15° C. The reaction was left to stir overnight at −5° C. This was followed by the addition of acetic anhydride (33 mg, 3.0 mmol). The reaction mixture was stirred for another 4 h at 22° C., and then worked up. Removal of the solvents at the reduced pressure, followed by a flash column chromatography of the impure material afforded pure 3 (193 mg, 60%). The analytical data for compound 3, obtained by this method corresponded to the data obtained by methods A and B as described above.

Example 2

1-α-D-(5'-O-(4-nitrobenzenesulfonyl)-2',3'-di-O-pivaloyl-arabinofuranosyl)-2-nitroimidazole (Dipivaloyl AZA nosylate, NsDiPiv-AZA; Pivaloyl nosyl AZA; 3a)

The synthesis of compound 3a was achieved by two methods A and B as shown in Scheme 1, and is described below.

Method A for Dipivaloyl AZA nosylate, 3a:

This synthesis route proceeded via following compounds.

1-α-D-[5'-O-Tert-butyldiphenylsilanoxyl-2',3'-di-O-trimethylacetylarabinofuranosyl]-2-nitroimidazole (1a)

Tert-butyl diphenylchlorosilane (0.25 ml, 0.97 mmol) was added drop wise to a solution of AZA (260 mg, 1.06 mmol) in 1.25 ml of pyridine. Follow the reaction mixture was stirred at room temperature for 24 h, trimethylacetyl chloride (0.5 ml, 4.05 mmol) was added dropwise. After the reaction mixture was stirred at room temperature for another 48 h, all solvents were evaporated in vacuo. The residue was purified by SiO$_2$ column chromatography using EtOAc/hexanes (1:4, v/v) as eluents to afford 1a (513 mg) as colorless syrup. $^1$H-NMR (CDCl$_3$, 300 MHz) δ 7.73~7.67 (m, 4H, Phenyl), 7.47~7.36 (m, 6H, Phenyl), 7.23 (d, $J_{4,5}$=1.0 Hz, 1H, H-5), 7.22 (d, $J_{5,4}$=1.0 Hz, 1H, H-4), 6.46 (d, $J_{2',1'}$=1.3 Hz, 1H, H-1'), 5.27 (d, $J_{1',2'}$=1.3 Hz, 1H H-2'), 5.14 (dd, $J_{2',3'}$=1.0 Hz, $J_{4',3'}$=2.1 Hz, 1H, H-3'), 4.52 (ddd, $J_{3',4'}$=2.1 Hz, $J_{5',4'}$=5.0 Hz, $J_{5'',4'}$=5.0 Hz, 1H, H-4'), 3.89 (dd, $J_{4',5'}$=5.0 Hz, $J_{gem}$=11.0 Hz, 1H, H-5'), 3.83 (dd, $J_{4',5'}$=5.0 Hz, $J_{gem}$=11.0 Hz, 1H, H'-5'), 1.12 (s, 9H, 3×CH$_3$), 1.10 (s, 9H, 3×CH$_3$), 1.09 (s, 9H, 3×CH$_3$) ppm; $^{13}$C-NMR (CDCl$_3$, 75 MHz) δ 176.6 (C=O), 176.1 (C=O), 146.0 (C-2), 135.7-132.9 (phenyl carbons), 129.9 (C-5), 127.8~127.7 (remaining phenyl carbons), 123.3 (C-4), 92.3 (C-1'), 88.1 (C-2'), 81.4 (C-3'), 77.4 (C-4'), 63.6 (C-5'), 38.6 (C(CH$_3$)$_3$), 26.9 (CH$_3$), 19.3 (SiC(CH$_3$)$_3$) ppm.

1-α-D-[5'-Hydroxy-2',3'-di-O-trimethylacetylarabinofuranosyl]-2-nitroimidazole (2a)

Compound 1a (500 mg, 0.8 mmol) was dissolved in of acetonitrile (25 ml), then benzoic acid (658.4 mg, 5.6 mmol) and potassium fluoride (325.8 mg, 5.6 mmol) were added to this solution. The reaction mixture was stirred at 80° C. for 12 h. The mixture was filtered and the solution was evaporated in vacuo. The residue was purified with SiO$_2$ column chromatography using EtOAc/hexanes (1:2, v/v) as eluent to afford 2a (220 mg) as syrup. $^1$H-NMR (CDCl$_3$, 300 MHz) δ 7.39 (d, $J_{4,5}$=1.0 Hz, 1H, H-5), 7.23 (d, $J_{5,4}$=1.0 Hz, 1H, H-4), 6.65 (d, $J_{2',1'}$=1.0 Hz, 1H, H-1'), 5.37 (d, $J_{1',2'}$=1.0 Hz, 1H, H-2'), 5.04 (dd, $J_{2',3'}$=1.0 Hz, $J_{4',3'}$=2.1 Hz, 1H, H-3'), 4.52 (ddd, $J_{3',4'}$=2.1 Hz, $J_{5',4'}$=5.3 Hz, $J_{5'',4'}$=5.3 Hz, 1H, H-4'), 3.94 (dd, $J_{4',5'}$=5.3 Hz, $J_{gem}$=9.0 Hz, 1H, H-5'), 3.90 (dd, $J_{4',5''}$=5.3 Hz, $J_{gem}$=9.0 Hz, 1H, H'-5'), 2.42 (s, 1H, OH), 1.28 (s, 9H, 3×CH$_3$), 1.10 (s, 9H, 3×CH$_3$) ppm; $^{13}$C-NMR (CDCl$_3$, 75 MHz) δ 177.3 (C=O), 176.3 (C=O), 146.0 (C-2), 129.9 (C-5), 123.3 (C-4), 93.2 (C-1'), 88.9 (C-2'), 81.7 (C-3'), 77.4 (C-4'), 62.4 (C-5'), 38.7 (C(CH$_3$)$_3$), 26.9 (CH$_3$) ppm.

1-α-D-[5'-O-(4-Nitrobenzenesulfonyl)-2',3'-di-O-trimethylacetylarabinofuranosyl]-2-nitroimidazole (Dipivaloyl AZA nosylate, NsDiPiv-AZA; Pivaloyl nosyl AZA; 3a Compound 2a (210 mg, 0.5 mmol) was dissolved in 10 mL of pyridine, 4-nitrobenzenesulfonyl chloride (221 mg, 1 mmol) and DMAP (6 mg, 0.05 mmol) was added. The reaction mixture was stirred at room temperature for 16 h. The solvent was evaporated in vacuum. The residue was purified by SiO$_2$ column chromatography using EtOAc/hexanes 1:4 (v/v) as eluent to afford 65 mg of 3a as syrup. $^1$H-NMR (CDCl$_3$, 300 MHz) δ 8.43 (d, $J_{3'',2''}$=$J_{5'',6''}$=6.72 Hz, 2H, Phenyl H-2", H-6"), 8.17 (d, $J_{2'',3''}$=$J_{6'',5''}$=6.72 Hz, 2H, Phenyl H-3", H-5"), 7.30 (s, 1H, H-5), 7.23 (s, 1H, H-4), 6.61 (d, $J_{2',1'}$=1.2 Hz, 1H, H-1'), 5.39 (d, $J_{1',2'}$=1.2 Hz, 1H, H-2'), 4.99 (dd, $J_{2',3'}$=1.2 Hz, $J_{4',3'}$=2.4 Hz, 1H, H-3'), 4.62 (ddd, $J_{3',4'}$=2.4 Hz, $J_{5',4'}$=5.5 Hz, $J_{5'',4'}$=5.5 Hz, 1H, H-4'), 4.42 (dd, $J_{4',5'}$=5.5 Hz, $J_{gem}$=11.0 Hz, 1H, H-5'), 4.39 (dd, $J_{4',5''}$=5.5 Hz, $J_{gem}$=11.0 Hz, 1H, H'-5'), 1.28 (s, 9H, 3×CH$_3$), 1.10 (s, 9H×CH$_3$) ppm; $^{13}$C NMR (CDCl$_3$) δ 26.82 and 26.86 (CH$_3$s from pivaloyl moieties), 38.63 and 38.82 (tert-C in pivaloyl moities), 68.43 (C-5'), 76.26 (C-4'), 81.06 (C-3'), 85.08 (C-2'), 93.30 (C-1'), 122.00 (imidazole C-4), 124.54 (phenyl C-3 and C-5), 124.58 (imidazole C-5), 129.38 (phenyl C-2 and C-6), 141.18 (phenyl C-1 and imidazole C-2), 151.02 (phenyl C-1), 176.17 (C=O at C-2'), 177.08 (C=O at C-3') ppm.

Method B for Dipivaloyl AZA Nosylate, 3a:

This route included the reaction of silver nosylate with 1-α-D-[5'-iodo-2',3'-di-O-trimethylacetylarabinofuranosyl]-2-nitroimidazole (Di-pivaloyl IAZA), 6 (the synthesis for 6 is described under Example II), and proceeded as below.

Silver 4-nitrobenzene sulfonate (3.01 g, 9.74 mmol) was dissolved in anhydrous acetonitrile (30 mL) and the mixture was added to dipivaloyl IAZA (1.5 g, 2.87 mmol), pre-contained in a round bottom flask, and the contents were stirred vigorously at 60° C. for 4 h. The reaction mixture was then filtered and the solvent was removed by rotary evaporation under reduced pressure. The residue was purified by flash silica gel column chromatography using ethyl acetate/hexanes (v/v; 1:3) to afford pure 3a (55 mg) as syrupy product along with unreacted dipivaloyl IAZA (1.0 g).

Example 3

1-α-D-(5'-O-toluenesulfonyl-2,3-di-O-trimethylacetylarabinofuranosyl)-2-nitroimidazole (TsDiPiv-AZA; Pivaloyl tosyl AZA, Pivaloyl AZA tosylate, Dipivaloyl AZA tosylate; 8)

This molecule was synthesized by methods A and C as described below.

Method A.

1-α-D-[5'-Hydroxyl-2',3'-di-O-trimethylacetylarabinofuranosyl]-2-nitroimidazole, 2a, (200 mg, 0.5 mmol) was dissolved in anhydrous pyridine (20 mL), stirred, and cooled to 0-5° C. Toluenesulfonylchloride (105 mg, 0.55 mmol) was added to it, and the contents were stirred. The temperature was allowed to warm up to 22° C., and the stirring was continued for an additional 24 h. Ice (3 mL) was added, and the solvents were evaporated under reduced pressure to afford impure mixture, which was chromatographed on a flash silica gel column (0.25% MeOH in $CH_2Cl_2$) to give 0.19 g (69%) of pure TsDiPiv-AZA as white crystals (m.p. 55-57° C.); $^1H$ NMR ($CDCl_3$) δ 1.09 (s, 9H, t-butyl group), 1.25 (s, 9H, t-butyl group), 2.46 (s, 3H, toluoyl $CH_3$), 4.24 (dd, $J_{4,5'}$=2.4 Hz, $J_{gem}$=7.3 Hz, 1H, H-5'), 4.28 (dd, $J_{5'',4'}$=4.5 Hz, $J_{gem}$=7.3 Hz, 1H, H-5''), 4.63 (ddd, $J_{3',4'}$=1.6, $J_{5',4'}$=2.4 Hz, $J_{5'',4'}$=4.5 Hz, 1H, H-4'), 4.98 (d, $J_{4',3'}$=1.6 Hz, 1H, H-3'), 5.33 (s, 1H, H-2'), 6.51 (s, 1H, H-1'), 7.22 (s, 1H, imidazole H-4), 7.31 (s, 1H, imidazole H-5), 7.38 (d, 2H, J=8.2 Hz, phenyl H-3 and H-5), 7.83 (d, 2H, J=8.2 Hz, phenyl H-2 and H-6) ppm; $^{13}C$ NMR ($CDCl_3$) δ 21.69 (tolyl $CH_3$), 26.83 and 26.87 (6×$CH_3$, two tert-butyl), 38.59 and 38.77 (2× carbons of tert-butyl), 67.71 (C-5'), 76.32 (C-4'), 81.15 (C-3'), 85.20 (C-2'), 93.31 (C-1'), 121.76 (imidazole C-4), 128.03 (phenyl C-3 and C-5), 128.53 (imidazole C-5), 129.96 (phenyl C-2 and C-6), 132.44 (C-1 phenyl), 145.36 (C-2, nitroimidazole), 145.36 (C, phenyl C-4), 176.05 (C=O at C-2'), 176.76 (C=O at C-3') ppm.

HPLC retention time: 50% $CH_3CN$/50% $H_2O$; 1.5 ml/min: 280 nm; 19.02 minutes.

Method C:

This method proceeded via following steps.

1-α-D-(5'-O-toluenesulfonylarabinofuranosyl)-2-nitroimidazole (7)

Toluenesulfonyl (tosyl) chloride (78.3 mg, 0.41 mmol) in pyridine (0.5 ml) was added to a stirred solution of α-AZA, 1, (100 mg, 0.41 mmol) in pyridine (2 ml) at −15° C. The reaction was left to stir overnight at −5° C. A second addition of tosyl chloride (40 mg, 0.21 mmol) in pyridine (0.5 ml) was added again at −15° C. and left to stir at 5° C. overnight. Ice (3 ml) was added then the solution was evaporated under reduced pressure to remove the pyridine. The crude product was dissolved in ethyl acetate (10 ml) and washed with water (3×10 ml). The organic layer was dried ($MgSO_4$) and evaporated under reduced pressure to give 0.17 g of impure product which was purified by flash column chromatography (0.75% MeOH in $CH_2Cl_2$) to give 0.09 g (55%) of pure Tosyl-AZA as white crystals; $^1H$ NMR ($CDCl_3$) δ 2.45 (s, 3H, tolyl $CH_3$), 4.00 (m, 1H, H-4'), 4.22 (m, 2H, H-5'), 4.90 (s, 2H, H-2' and H-3'), 6.26 (s, 1H, H-1'), 7.10 (s, 1H, imidazole H-4), 7.93 (d, 2H, phenyl H-3 and H-5, J=8.0 Hz), 7.58 (s, 1H, imidazole H-5), 7.82 (d, 2H, phenyl H-2 and H-6, J=8.0 Hz) ppm.

1-α-D-(5'-O-toluenesulfonyl-2',3'-di-O-trimethylacetylarabinofuranosyl)-2-nitroimidazole (TsDiPiv-AZA, Dipivaloyl AZA tosylate, Pivaloyl tosyl AZA, Pivaloyl AZA tosylate; 8)

Trimethylacetyl (pivaloyl) chloride (60.2 mg, 61.5 μL, 0.50 mmol, 2.5 eq) was added to a stirred solution of 7, (80.0 mg, 0.20 mmol) in pyridine (3 ml) at −15° C. The reaction was left to stir overnight at −5° C. A second addition of trimethylacetyl chloride (12.0 mg, 12.3 ml, 100 μmol) was again added at −15° C. and left to stir at −5° C. for 24 hours. Ice (3 ml) was added then the solution was evaporated under reduced pressure to remove the pyridine. The crude product was dissolved in ethyl acetate (5 ml) and washed with water (3×5 ml). The organic layer was dried ($MgSO_4$) and evaporated under reduced pressure to give 0.90 g of crude product. The crude material was purified by flash column chromatography (0.25% MeOH in $CH_2Cl_2$) to give 0.070 g (62%) of pure TsDiPiv-AZA as white crystals. The analytical and spectral data for 8 obtained by this method corresponded to the data obtained by method A, and confirmed the formation of this compound.

Example II of General Formula 1

1-α-D-[5'-Iodo-2',3'-di-O-trimethylacetylarabinofuranosyl]-2-nitroimidazole (Di-pivaloyl IAZA; 6)

1-α-D-(5'-iodo-5'-deoxyarabinofuranosyl)-2-nitroimidazole (α-IAZA) (1.10 g, 2.88 mmol) was dissolved in pyridine (100 mL) and trimethylacetyl chloride (2.7 g, 14.1 mmol) was added drop wise to this solution under stirring. The mixture was stirred at room temperature for 30 h, and then the solvent was removed in vacuo. The viscous residue, so obtained, was purified by flash silica gel column chromatography using ethyl acetate/hexanes (1:4; v/v) to afford pure product as syrup. Yield 1.49 g. (90%); $^1H$-NMR ($CDCl_3$, 300 MHz) δ 7.39 (d, $J_{4,5}$=1.2 Hz, 1H, H-5, imidazole), 7.23 (d, $J_{5,4}$=1.2 Hz, 1H, H-4, imidazole), 6.67 (d, $J_{2',1'}$=1.2 Hz, 1H, H-1'), 5.37 (d, $J_{2',1'}$=1.2 Hz, 1H, H-2'), 5.16 (dd, $J_{2',3'}$=1.2 Hz, $J_{4',3}$=1.8 Hz, 1H, H-3'), 4.65 (ddd, $J_{3',4'}$=1.8 Hz, $J_{5',4'}$=7.3 Hz, $J_{5'',4'}$=7.3 Hz, 1H, H-4'), 3.47 (dd, $J_{4',5'}$=7.3 Hz, $J_{gem}$=11.0 Hz, 1H, H-5'), 3.41 (dd, $J_{4',5''}$=7.3 Hz, $J_{gem}$=11.0 Hz, 1H, H'-5') ppm; $^{13}C$-NMR ($CDCl_3$, 75 MHz) δ 176.6 (C=O), 175.9 (C=O), 148.0 (C-2), 130.1 (C-5), 123.3 (C-4), 93.4 (C-1'), 87.7 (C-2'), 81.5 (C-3'), 78.1 (C-4'), 38.6 (C-5'), 26.9 ($CH_3$), 2.10 ($C(CH_3)_3$) ppm.

Radiochemistry.

Radiofluorination was performed in a GE TracerLab FDG FX™ automated synthesizer. $^{18}F$-Fluoride was delivered from the target on to a QMA Accel trapping cartridge, preconditioned with 0.5 M $NaHCO_3$, and was trapped as $Na^{18}F$. Elution of this fluoride was done by a solution of $K_2CO_3$/K2.2.2 solution (3.5 mg:15 mg in 100 μL $H_2O$/900 μL anhydrous acetonitrile, respectively) followed by two azeotropic dryings of this complex at 70° C. using acetonitrile. The AZA precursor, under investigation, was dropped in to the reactor as a solution in anhydrous DMSO (1.0 mL) and, depending on the precursor, was reacted at 100° C. for 5-10 min. This was followed by the removal of protective groups (acetyl or pivaloyl) from the radiofluorinated intermediate by alkaline hydrolysis using 0.1N NaOH solution for 2 min at 30° C. The pH of the reaction mixture was neutralized by adding 0.9 mL of 0.4M NaH$_2$PO$_4$ aqueous solution and the whole mixture was dispensed to the HPLC injector (7 mL loop size) for the chromatographic purification.

HPLC Purification.

Post-labeling mixture was subjected to HPLC purification process. The instrumentation, control systems and connections used for this process consisted of Beckman "Gold Plus" integrated pumps/Model Number 126 and Beckman 32 Karat/Version 3.0 software, HPLC RP Phenomenex Nucleosil 10μ C$_{18}$ 100 A Column (25×1.0 cm) and a Phenomenex LUNA 5μ C$_{18}$ 100 A Column (5.0×1.0 cm). Eluent for HPLC purification, composed of 8% ethanol and 92% sterile water for injection (SWFI), was run at a flow rate of 2.0 mL/min. Radiolabeled $^{18}$F-FAZA was identified by a dual detection technique that used UV absorption (λmax 320 ηm) and corresponding radioactive peak at same retention time. The radiochemical identity of the peak corresponding to $^{18}$F-FAZA was confirmed by injecting standard FAZA prior to the purification of radiolabeled mixture under same elution conditions that appeared at a retention time of 26 (±5%). Impure labeled mixture was also checked by tlc 'co-spot' chromatography (2.5×7.5 silica gel micro tlc plates using EtOAc as developing solvent) to obtain exact composition of the radiochemical mixture and determine the losses that happen during the HPLC purification.

Post-Purification Quality Control (QC).

The radiochemical identity and the purity of purified $^{18}$F-FAZA were confirmed by tlc chromatography. A tlc plate was spotted with standard FAZA (left), a co-spot of standard FAZA and purified $^{18}$F-FAZA (middle), and only purified $^{18}$F-FAZA (right side of the plate), air dried, and then developed by EtOAc. The Rf of standard FAZA was determined by a UV absorption while the Rf of the radioactive $^{18}$F-FAZA was checked using AR 2000 Bioscan TLC scanner. The Rf of both standard FAZA and corresponding radioactive product appeared at same distance (±0.05). The radiochemical purity of $^{18}$F-FAZA always ranged >95%.

Results and Discussion

Three new precursors, diacetyl AZA nosylate, 3, dipivaloyl AZA nosylate, 3a, and dipivaloyl AZA tosylate, 8, were designed in the class of compounds described in this invention to overcome the formation of secondary products during the radiofluorination that is encountered during the radiofluorination with AZA tosylate. Thermal deacetylation in nucleosides is a common phenomenon when the reactions are performed at elevated temperature (>70° C.) (29). It leads to poor fluorination not only due to the formation of intramolecular oxirane rings to give 2',3'-anhydro AZA tosylate and 2',5'-anhydro AZA but also leads to the intramolecular hydrogen bond between neighboring tosyl moiety and deacetylated OH function. In addition, the carbons at –2' and –3' positions in arabinofuranose nucleus and the nitro group at C-2 position in the 2-nitroimidazole nucleus, being nucleophilic centre, are also prone to the attack by the fluoride leading to the possibility of formation of several fluorine substituted product (30). Indeed, it was observed that additional radiofluorinated species are formed when $^{18}$FAZA is synthesized from the AZA tosylate. Therefore, the radiofluorination profiles of two new FAZA precursors was explored, AZA nosylate that might have a faster substitution rate due to more pronounced nucleophilic properties in comparison to the tolyl group, and pivaloyl AZA tosylate which is thermally more stable and would therefore minimize the formation of oxirane related secondary products and, thus, provide a superior labeling quality of the mixture and the radiochemical yield.

Description of Diacetyl AZA Nosylate, 3, Synthesis by Methods A, B and C and Dipivaloyl AZA Nosylate, 3a, by Methods A and B and Dipivaloyl AZA Tosylate, 8, by Methods A and C

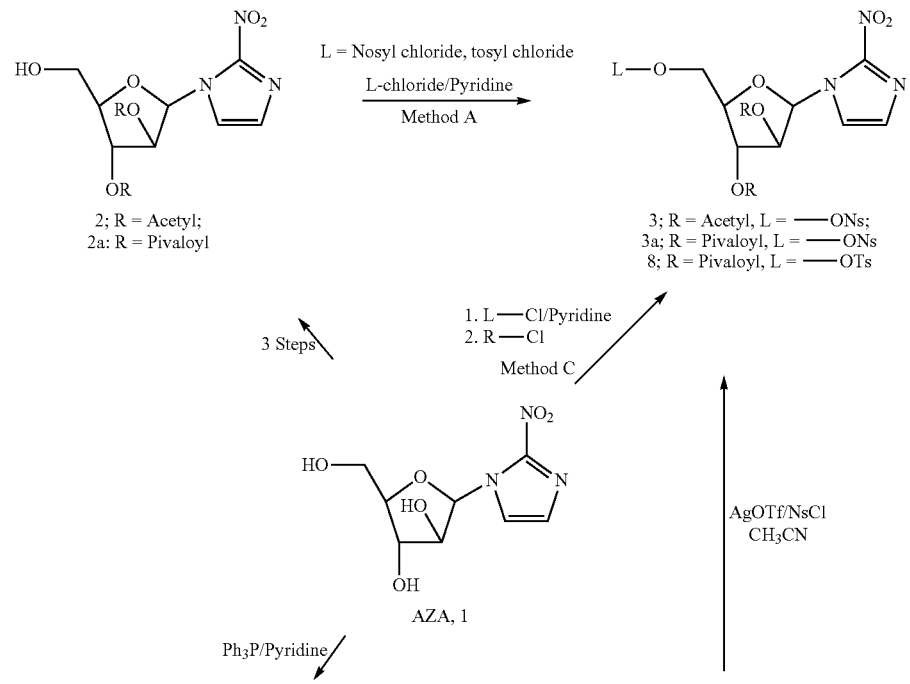

Scheme 1. Synthesis of di-O-acetyl AZA nosylate, 3, via Methods A, B and C, and di-O-pivaloyl AZA nosylate via methods A and B.

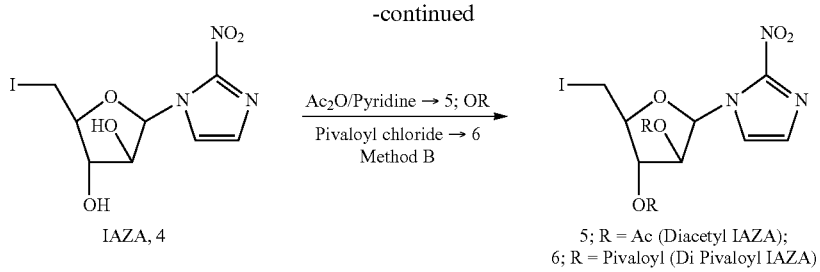

IAZA, 4

5; R = Ac (Diacetyl IAZA);
6; R = Pivaloyl (Di Pivaloyl IAZA)

Trimethylacetyl (pivaloyl)ethers provide similar electronic atmosphere to the molecule as do the acetyl groups (32), and are also reported to be more stable at higher temperatures (33). The development of 5'-O-tosylated/nosylated precursors with trimethylacetyl protective group at 2'- and 3'-OH groups would be an adequate replacement of the current FAZA (and IAZA) precursor, tosyl AZA, since it will also not alter the basics of the manufacturing process, which requires an alkaline hydrolysis of radiofluorinated product. The synthesis of 2',3'-di-O-trimethylacetyl-5'-O-toluenesulfonyl AZA, 8, and 2',3'-di-O-trimethylacetyl-5'-O-(4-nitrobenzene)sulfonyl AZA, 3a, started from AZA, 1, (34) which was selectively tosylated/nosylated, respectively, at 5'-OH group in anhydrous pyridine at 22° C. This tosylated, 7, /nosylated, 7a, intermediate was treated with a solution of trimethylacetyl chloride in anhydrous pyridine at −5° C. for 24 h to afford 8 (62% yield) and 3a (65% yield), respectively (Scheme 2).

Scheme 2.
Synthesis of Pivaloyl AZA tosylate, 8, and Pivaloyl AZA nosylate, 3a.

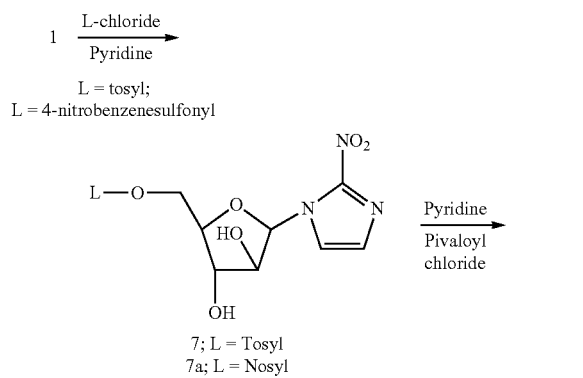

Scheme 3. Radiofluorination of the precursers 3 and 8.

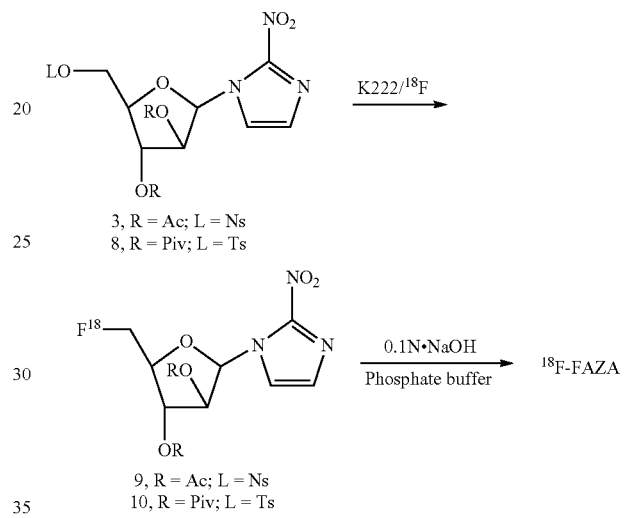

3, R = Ac; L = Ns
8, R = Piv; L = Ts

9, R = Ac; L = Ns
10, R = Piv; L = Ts

Radiofluorination of the precursors was performed using conditions that have been previously been shown to be compatible with commercially available automated synthesizers, such as the GE Tracerlab, that are used in the generation of PET radiotracers for diagnostic and therapeutic applications (28). The labeling for these precursors was attempted at the temperatures ranging between 90-105° C. since the optimized yield for $^{18}$F-FAZA from its diacetyl AZA tosylate precursor is reported best at 100° C. (28). The experimental data are provided in Table 1. The skilled worked will appreciate that alternate methods of fluorination may used.

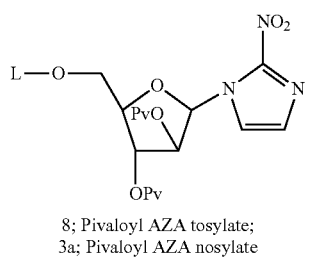

8; Pivaloyl AZA tosylate;
3a; Pivaloyl AZA nosylate

Novel FAZA and IAZA precursors 3 and 8 were radiolabeled according to the methods described in scheme 3.

TABLE 1

Radiofluorination yields of $^{18}$F-FAZA from the precursors 3 and 8.

| Precursors | Amount (mg) | Temp. (° C.) | RCY (%) | Time (min) | Solvent |
|---|---|---|---|---|---|
| DiPiv AZA Tosylate | | | | | |
| Reaction 1 | 5 | 100 | 33.1 | 5 | DMSO |
| Reaction 2 | 5 | 100 | 57.4 | 5 | DMSO |
| Reaction 3 | 5 | 100 | 54.6 | 5 | DMSO |
| Reaction 4 | 5 | 105 | 14.6 | 5 | DMSO |
| Reaction 5 | 5 | 105 | 57.4 | 5 | DMSO |
| Reaction 6 | 5 | 105 | 53.6 | 5 | DMSO |
| Reaction 7 | 5 | 105 | 51.3 | 5 | DMSO |
| Reaction 8 | 10 | 105 | 42.5 | 5 | DMSO |
| Reaction 9 | 10 | 105 | 19.9 | 5 | DMSO |
| Reaction 10 | 10 | 100 | 2.4 | 5 | CH$_3$CN |

TABLE 1-continued

Radiofluorination yields of $^{18}$F-FAZA from the precursors 3 and 8.

| Precursors | Amount (mg) | Temp. (° C.) | RCY (%) | Time (min) | Solvent |
|---|---|---|---|---|---|
| Diacetyl AZA Nosylate | | | | | |
| Reaction 11 | 5 | 90 | 37.9 | 5 | DMSO |
| Reaction 12 | 5 | 90 | 59.9 | 5 | DMSO |
| Reaction 13 | 5 | 95 | 79.9 | 10 | DMSO |
| Reaction 14 | 5 | 100 | 43.2 | 5 | DMSO |
| Reaction 15 | 5 | 100 | 53.7 | 5 | DMSO |

The tlc chromatograms of unpurified post-labeling reaction mixtures from the precursors 3 and 8 (FIGS. 2a, b) were acquired and their Rfs were compared with standard FAZA (co-spotting) to analyze the radiofluorination yield of $^{18}$F-FAZA from new precursors.

It can be seen that both nosylate (precursor 3, FIG. 2b, Reaction 13, Table 1) and pivaloyl tosylate (precursors 8, FIG. 2a, Reaction 8, Table 1) offered much better radiochemical yields and cleaner chemical and radiochemical profiles for the reaction mixtures from these precursors in comparison to the current diacetyl AZA-tosylate precursor (commercially available) that may offer a cartridge-based purification of the [$^{18}$F]FAZA. Using diacetyl AZA nosylate 3, the RCYs for $^{18}$F-FAZA were superior (up to 80%, uncorrected, FIG. 2b, Reaction 13) in comparison to the corresponding pivaloyl precursor 8 (FIG. 2a Reaction 10). It was also observed that the radiochemical yields from the dipivaloyl AZA tosylate precursor 8 did not alter too much (except reactions 4 and 9) with the variation in the reaction temperature however the nosylate precursor 3 was affected by small changes (±5° C.).

Figure 2:
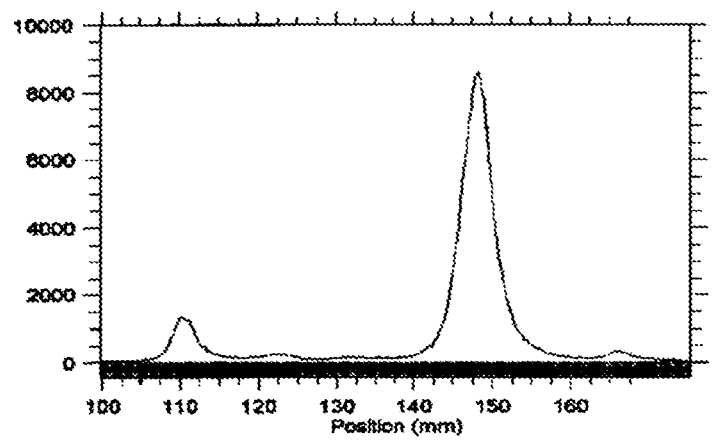
FIG. 2 depicts a) an example of TLC radiochromatography of the unpurified radiofluorinated reaction mixtures from di-O-acetyl AZA nosylate (95° C., 10 min in DMSO, 80% of $^{18}$F-FAZA is present, b) purified $^{18}$F-FAZA.
Figure 2:
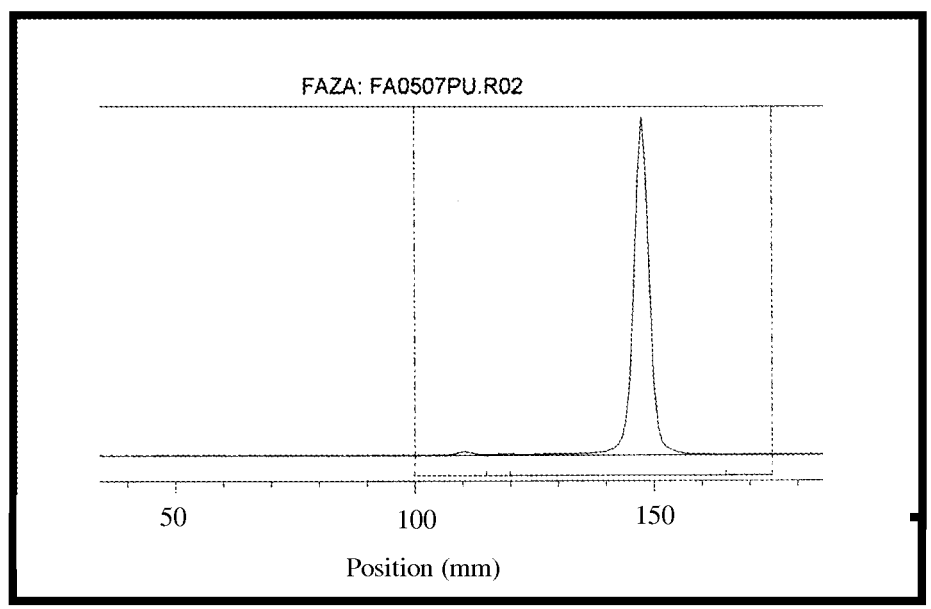

FIG. 2 depicts examples of TLC radiochromatography of the unpurified radiofluorinated reaction mixtures from a) di-O-acetyl AZA nosylate (95° C., 10 min in DMSO, ~80% of F-18 FAZA is present, Lot # FANS0708) and; b) the purified $^{18}$F-FAZA.

The HPLC-radiochromatography-based profile of the reaction mixtures from the novel precursors 3 (FIG. 3A) and 8 (FIG. 3B) reveal that the formation of secondary products, pre- and post-FAZA elution (at retention times 15-28.5 min), is minimal in comparison to when radiofluorination is attempted from DiAcTs AZA (FIG. 3C). Synthesis of [$^{18}$F] FAZA from its current precursor AZA tosylate leads to additional recovery losses since several secondary products are formed near FAZA region that minimize its collection (FIG. 3C). Additional radiofluorinated products are also seen in significant quantity from the reaction mixture of DiAcTs AZA at late (after FAZA is eluted) retention times (~40 and ~54 min) with a slow elution pattern. This has been minimized in case of $^{18}$F-FAZA reaction mixture obtained from 3 and 8 which improves both radiochemical yields, reduces the purification complicacy that is faced due to the formation of side products in currently used labeling procedure, and enables a simpler and facilitated recovery of pure $^{18}$F-FAZA without any additional losses of radioactivity (FIGS. 3A, 3B).

Figure 3:
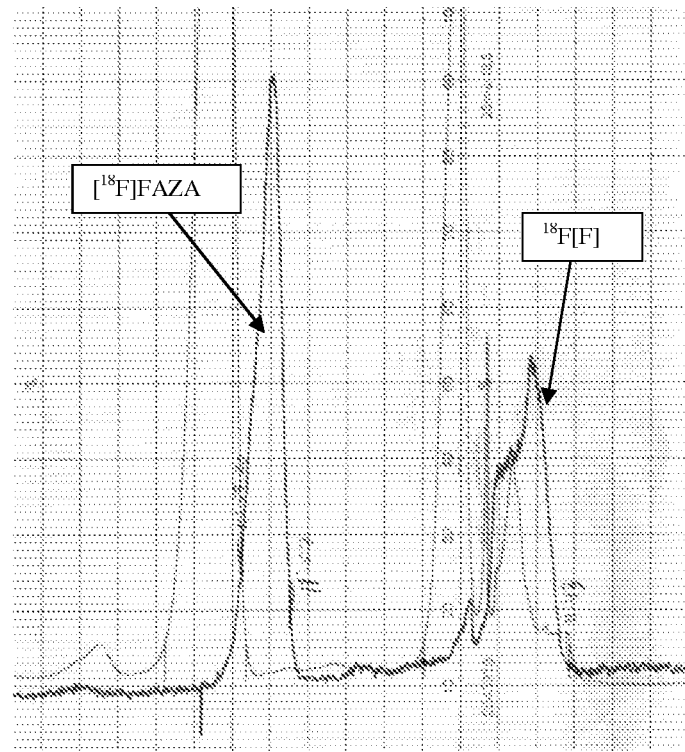
FIG. 3 depicts an HPLC profile of impure $^{18}$F-FAZA reaction mixture from A) pivaloyl AZA tosylate, 7, and B) diacetyl AZA nosylate, 3, indicating mainly unreacted $^{18}$F-fluoride, $^{18}$F-FAZA and demonstrating fewer side products in comparison to the mixture obtained from the tosylate precursor C) that is being currently used for the clinical manufacturing.
Figure 3:
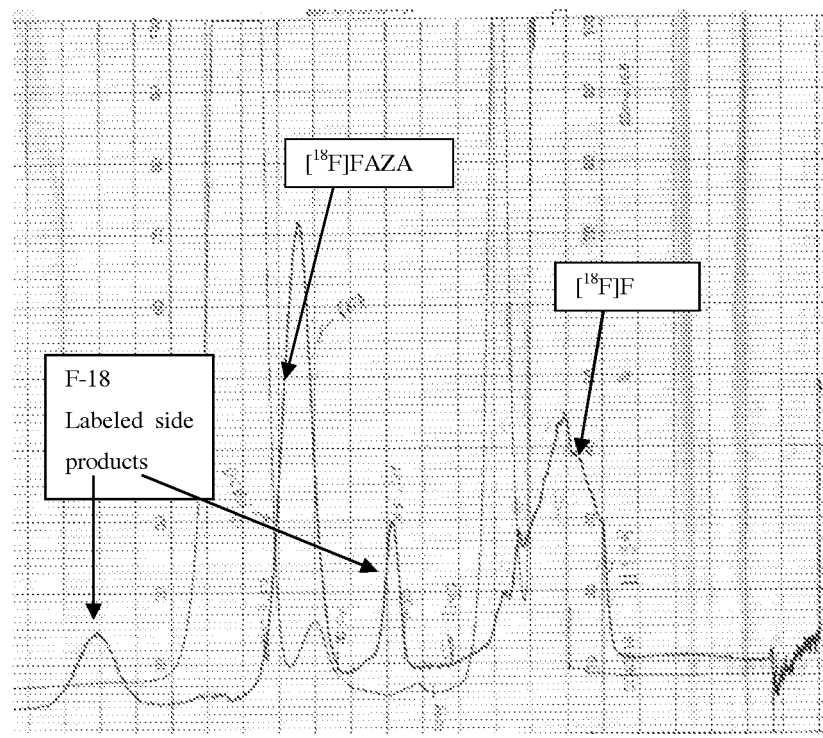
Figure 3:
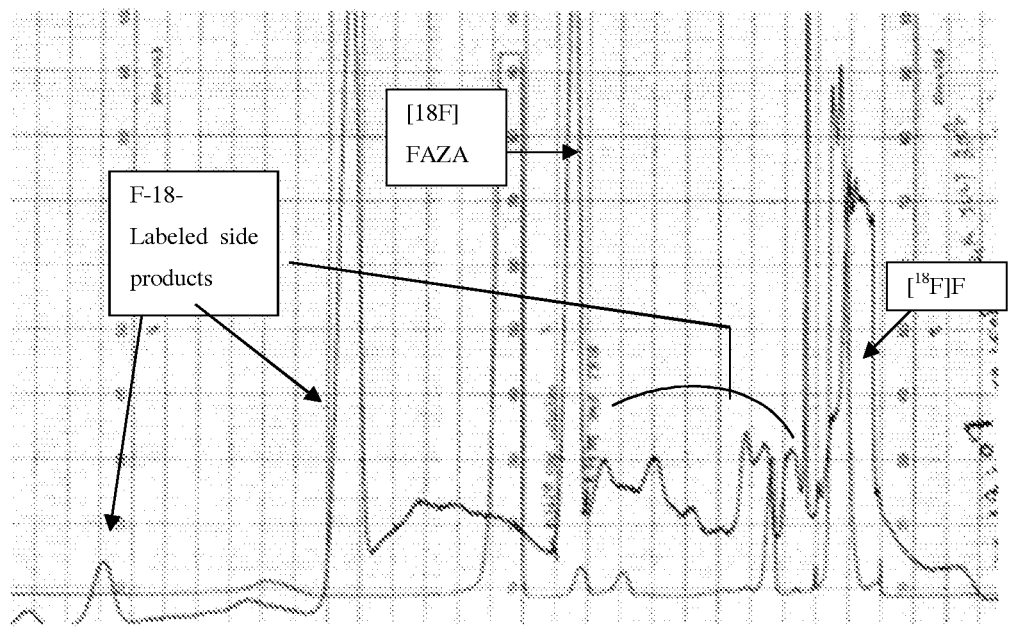

FIG. 3 depicts HPLC profile of impure FAZA reaction mixture from A) dipivaloyl AZA tosylate, 8, and B) diacetyl AZA nosylate, 3, indicating mainly unreacted $^{18}$F-fluoride, $^{18}$F-FAZA and demonstrating lesser side products in comparison to the mixture obtained from the tosylate precursor (C) that is being used currently for the clinical manufacturing UV signals in HPLC chromatograms of the two mixtures (FIGS. 3A and B) also demonstrate that the formation of radiochemical and chemical side products at retention times ~14-28.5 min is much lesser in the reaction mixtures obtained from radiofluorination of 3 and 8 in comparison to the reaction mixture obtained from DiAcTs AZA (FIG. 3C).

CONCLUSIONS

The stability of the precursor plays an important role in the quality of final product and the reaction mixture. Its instability during the radiofluorination may lead to additional labeled species besides the desired product which would result in to significantly reduced yields of the desired product ($^{18}$F-FAZA) and make its purification complicated, more so, when the labeled isotope has a short half life. The labeling of $^{18}$F-FAZA using 5'-O-Ts-2',3'-diacetyl AZA led to several additional labeled species, most likely, due to the reaction of fluoride with newly generated tosylates that are formed due to thermal deacetylation of the original tosylate precursor. The possibility of the formation of a C-2 fluoro-AZA product that may happen due to the nucleophilic displacement of C-2-nitroimidazole group in the diacetyl tosyl AZA can also not be ruled out. Although not identified, but the chromatogram of AZA tosylate reaction mixture (FIG. 3C) demonstrates other radiolabeled species. This process is not observed with dipivaloyl AZA tosylate since thermal deblocking is not reported with pivaloyl substituted precursors at this temperature. As a result, side products' formation is minimal when dipivaloyl tosyl AZA is used as a precursor and leads to a less complicated HPLC purification of $^{18}$F-FAZA. Pivaloyl-based AZA tosylate and nosylate appear to be the better precursors among this class of the precursors for $^{18}$F-FAZA labeling due to minimal side products formation. These precursors, and the reagents and conditions used to convert them to radiolabeled FAZA, are compatible for inclusion in kits that are used in commercial automated synthesizer units, such as the GE Tracerlab, which are used to generate PET radiotracers for diagnostic and therapeutic applications. This invention demonstrates its application and potential in the development of other labeled compounds belonging to this class of compounds and related molecules as described in the current invention.

REFERENCES

[1]. Vaupel P. Hypoxia and aggressive tumor phenotype: implications for therapy and prognosis. Oncologist. 2008; 13:21-6.
[2]. Nordsmark M, M Hoyer, J Keller, O S Nielsen, O M Jensen, J. Overgaard. The relationship between tumor oxygenation and cell proliferation in human soft tissue sarcomas. Int J Radiat Oncol Biol Phys. 1996; 35:701-08.
[3]. Nordsmark M, J Alsner, J Keller, O S Nielsen, O M Jensen, M R Horsman, et al. Hypoxia in human soft tissue sarcomas: adverse impact on survival and no association with p53 mutations. Br J. Cancer. 2001; 84:1070-75.
[4]. Nordsmark M, S M Bentzen, V Rudat, D Brizel, E Lartigau, P Stadler, et al. Prognostic value of tumour oxygenation in 397 head and neck tumors after primary radiation therapy. An international multi-center study. Radiother Oncol. 2005; 77:18-24.
[5]. Lee N Y, Q T Le. New developments in radiation therapy for head and neck cancer: intensity modulated radiation therapy and hypoxia targeting. Semin Oncol. 2008; 35:236-50.
[6]. Brown J M, A J Giaccia. The unique physiology of solid tumors: opportunities (and problems) for cancer therapy. Cancer Res. 1998; 58: 1408-16.

[7]. Chapman J D. Measurement of tumor hypoxia by invasive and non-invasive procedures: a review of recent clinical studies. Radiother Oncol. 1991; 20:13-19.

[8]. Wiebe L I, D Stypinski. Pharmacokinetics of SPECT radiopharmaceuticals for imaging hypoxic tissues. Q J Nucl Med. 1996; 40:270-84.

[9]. Bentzen L, S Keiding, M R Horsman, L Falborg, S B Hansen, J. Overgaard. Feasibility of detecting hypoxia in experimental mouse tumours with 18F-fluorinated tracers and positron emission tomography—a study evaluating [18F]Fluoro-2-deoxy-D-glucose. Acta Oncol. 2000; 39:629-37.

[10]. Tubis M, G T Krishnamurthy, J S Endow, R A Stein, R Suwanik, W H Bland. Labeled metronidazoles as potential new agents for amebic hepatic abscess imaging. Nucl Med (Stuttg). 1975; 14:163-71.

[11]. Chapman JD, A J Franko, J. Sharplin. A marker for hypoxic cells in tumours with clinical applicability. Brit J. Cancer. 1981; 43:546-50.

[12]. Wiebe L I, R H Mannan, J R Mercer, G W Haverland, J D Chapman. Structure-activity relationships among nitroimidazole nucleosides used as markers of tissue hypoxia. 7th Int Symp Radiopharmacol. Boston (1991).

[13]. Wiebe L. I. PET Radiopharmaceuticals for Metabolic Imaging in Oncology. In: PET and Molecular Imaging: State of the art and future perspectives.—N. Tamaki and Y. Kuge (Eds). International Congress Series. 2003:1264 C, 53-76.

[14]. Wiebe L I, A J B McEwan. Scintigraphic imaging of focal hypoxic tissue: development and clinical applications of 123I-IAZA. Brazilian Arch Biol Technol. 2002:45, S89-102.

[15]. Machulla H-J. (Ed.). Imaging of Hypoxia—Tracer Developments. Kluwer Academic Publishers, Dordrecht (1999).

[16]. Wiebe L I, D Stypinski. Pharmacokinetics of SPECT radiopharmaceuticals for imaging hypoxic tissues. Quart J Nucl Med. 1996;39, 270-284.

[17]. Nunn A, K Linder, H W Strauss. Nitroimidazoles and imaging hypoxia. Europ J Nucl Med. 1995:22, 265-280.

[18]. Kumar P, D Stypinski, H Xia, A J B McEwan, H J Machulla, L I Wiebe. Fluoroazomycin arabinoside (FAZA): Synthesis, 211 and 311-labelling and preliminary biological evaluation of a novel 2-nitroimidazole marker of tissue hypoxia. J Label Comp Radiopharmaceuticals. 1999; 42:3-16.

[19]. Bentzen L, S Keiding, M R Horsman, L Falborg, S B Hansen, J. Overgaard. Feasibility of detecting hypoxia in experimental mouse tumours with 18F-fluorinated tracers and positron emission tomography—a study evaluating [18F]Fluoro-2-deoxy-D-glucose. Acta Oncol. 2000; 39:629-637.

[20]. Postema E J, A J B McEwan, T A Riauka, P. Kumar, D. Richmond, L I Wiebe. Hypoxia imaging using 1-α-d-(5-deoxy-5-[18F]-fluoroarabinofuranosyl)-2-nitroimidazole (18F-FAZA): The initial results of Phase I/II study. Eur. J. Nucl. Med. Mol. Imaging. Published May, DOI 10.107/s00259-009-1154-5, 2009.

[21]. Piert M, H J Machulla, M Picchio, G Reischl, S Ziegler, P Kumar, H J Wester, R Beck, A J McEwan, L I Wiebe, M Schwaiger. Hypoxia-specific tumor imaging with 18F-fluoroazomycin arabinoside. J Nucl Med. 2005; 46:106-113.

[22]. Sorger D, M Patt, P Kumar, L I Wiebe, H Barthel, A Seese, C Dannenberg, A Tannapfel, R Kluge, O Sabri. [18F]Fluoroazomycinarabinofuranoside (18FAZA) and [18F]Fluoromisonidazole (18FMISO): a comparative study of their selective uptake in hypoxic cells and PET imaging in experimental rat tumors. Nucl Med. Biol. 2003; 30:317-326.

[23]. Hicks et al, Unpublished.

[24]. Beck R, B Röper, J M Carlsen et al. Pretreatment 18F-FAZA PET predicts success of hypoxia-directed radiochemotherapy using tirapazamine. J Nucl Med. 2007; 48:973-980.

[25]. http://clinicaltrials.govict/show/NCT00388687. Medical University of Vienna, Austria. 2006.

[26]. Souvatzoglou M, A Grosu, B Röper, B Krause, R Beck, G Reischl, M Picchio, H-J Machulla, H-J Wester, M Piert. Tumour hypoxia imaging with [18F]FAZA PET in head and neck cancer patients: a pilot study. Eur. J. Nucl. Med. Mol. Imaging., 2007:34(10), 1566-75.

[27]. http://clinicaltrials.govict/showNCT00323076. Cross Cancer Institute, Edmonton, Canada. 2007.

[28]. Reischl G, W Ehrlichmann, C Bieg, P Kumar, L I Wiebe, H.-J. Machulla. Preparation of the Hypoxia Imaging PET tracer [18F]FAZA: Reaction Parameters and Automation. Applied Radiat. Isotopes. 2005; 62:897-901.

[29]. Kunesch N, C Meit, J. Poisson. Tet. Lett. 1987; 28:3569.

[30]. Kumar P, S Emami, A J B McEwan, L I Wiebe. Development of an economical, single step synthesis of FAZA, a clinical hypoxia marker, and potential synthons to prepare its positional analogues. Lett. In Drug Design & Develop. 2009:6, 82-85.

[31]. Kumar, P. et al. Unpublished.

[32]. Nicolau K C, S E Webber. Synthesis. 1986; 453.

[33]. Nakano T, Y Ito, T Ogawa. Carbohydr. Res. 1993; 243: 43.

[34]. Kumar P, E Atrazheva, M Tandon, L I Wiebe. An improved synthesis of α-AZA, α-AZP and α-AZG, the precursors to clinical markers of tissue hypoxia. Tetrahedron Lett. 2001:42, 2077-2078.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The embodiments of the invention in which an exclusive property or privilege is claimed are defined as follows:

1. A compound having the structure of the formula,

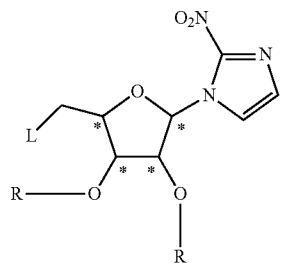

wherein the chiral centres may be (R) or (S) configuration;
L=halogen, (2-, 3-, or 4-nitrophenyl)sulfonyloxy, alkylsulfonyloxy, perfluoroalkylsulfonyloxy, phenylsulfonyloxy, substituted alkylsulfonyloxy, or substituted arylsulfonyloxy; and R is H, —$CH_2C(C=O)C_{1-5}$alkyl, —$CH_2C(=O)$Ph, $CH_2C(=O)$Caryl, —$CH_2C(=O)C_{1-5}$aralkyl, —$CH_2OC_{1-5}$alkyl, acetyl, -pivaloyl, -allyl, -allyloxycarbonyl, -benzyl, -benzyloxycarbonyl, -benzyloxymethyl, -tert-butoxycarbonyl, -tert-butyl, -tert-butyldimethylsilyl, -tert-butyldiphenylsilyl, -tert-butylmethylsilyl, -chloroacetyl, -diethylisopropylsilyl, -3,4-dimethoxybenzyl, -levulinoyl, -methylacetyl, -4-methoxybenzyl, -4-methoxybenzyloxymethyl, -2-methoxymethyl, -2-methoxyethoxymethyl, -methylthiomethyl, -4-nitrobenzyloxycarbonyl, -tetrahydropyran-2-yl, -thexyldimethylsilyl, -2,2,2-trichloroethoxycarbonyl, -triethylsilyl, -triisopropylsilyl, -trimethylsilyl, -2-(trimethylsilyl)ethoxycarbonyl, -3-(trimethylsilyl)ethoxymethyl, -triphenylsilyl or -trityl; or —$C(=O)R^1$, wherein $R^1$ is alkyl, aryl, aralkyl, heteroaryl, or heterocyclic; and wherein when L=halogen or 4-tosylsulfonyloxy R is not H or acetyl.

2. The compound of claim 1, wherein said compound is 1-α-D-(5'-O-(4-nitrobenzenesulfonyl)-2',3'-di-O-acetyl-arabinofuranosyl)-2-nitroimidazole.

3. The compound of claim 1, wherein said compound is 1-α-D-[5'-O-(4-nitrobenzenesulfonyl)-2',3'-di-O-trimethylacetylarabinofuranosyl]-2-nitroimidazole.

4. The compound of claim 1, wherein said compound is 1-α-D-(5'-O-toluenesulfonyl-2,3-di-O-trimethylacetylarabinofuranosyl)-2-nitroimidazole.

5. A method of making an imaging or therapy or radiotherapy agent, comprising reacting a compound or salt of claim 1, with a radionuclide.

6. The method of claim 5, wherein said radionuclide is a radiohalogen or a radioiodine.

7. The method of claim 6, wherein said radiohalogen comprises F-18.

8. The method of claim 6, wherein said radioiodine comprises I-123, I-124, I-125, or I-131.

9. A kit for the manufacture of an imaging or therapy or radiotherapy agent, comprising:
a compound of claim 1; and
instructions for the use thereof.

10. The kit of claim 9 wherein said imaging or therapy or radiotherapy agent is FAZA or IAZA.

11. The kit according to claim 10, wherein said imaging or therapy or radiotherapy agent is suitable for manufacture using an automated radio-synthesis unit.

* * * * *